US012653755B2

(12) United States Patent
Aerts et al.

(10) Patent No.: US 12,653,755 B2
(45) Date of Patent: Jun. 16, 2026

(54) ESKETAMINE FORMULATIONS AND METHODS FOR PREPARATION AND STORAGE

(71) Applicant: Janssen Pharmaceutica NV, Beerse (BE)

(72) Inventors: Caroline Anne Aerts, Beerse (BE); Kris Kayens, Beerse (BE); Koen Maria Schrijnemakers, Beerse (BE); Mohamedilias Jimidar, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 932 days.

(21) Appl. No.: 17/783,744

(22) PCT Filed: Dec. 14, 2020

(86) PCT No.: PCT/EP2020/086039
§ 371 (c)(1),
(2) Date: Jun. 9, 2022

(87) PCT Pub. No.: WO2021/116498
PCT Pub. Date: Jun. 17, 2021

(65) Prior Publication Data

US 2023/0058618 A1 Feb. 23, 2023

Related U.S. Application Data

(60) Provisional application No. 62/947,387, filed on Dec. 12, 2019.

(51) Int. Cl.

| | |
|---|---|
| ***A61J 1/06*** | (2006.01) |
| ***A61K 9/00*** | (2006.01) |
| ***A61K 31/135*** | (2006.01) |
| ***A61K 47/12*** | (2006.01) |

(52) U.S. Cl.
CPC ............. *A61J 1/065* (2013.01); *A61K 9/0043* (2013.01); *A61K 31/135* (2013.01); *A61K 47/12* (2013.01)

(58) Field of Classification Search
CPC ..... A61J 1/065; A61K 9/0043; A61K 31/135; A61K 47/12; A61K 9/08; A61K 47/183
See application file for complete search history.

(56) References Cited

U.S. PATENT DOCUMENTS

| | | | |
|---|---|---|---|
| 2003/0082214 A1 | 5/2003 | Williams et al. | |
| 2014/0275276 A1* | 9/2014 | Basstanie | A61K 47/26 514/646 |
| 2016/0338977 A1 | 11/2016 | Singh et al. | |
| 2019/0117591 A1 | 4/2019 | Basstanie et al. | |

FOREIGN PATENT DOCUMENTS

| | | |
|---|---|---|
| JP | 2005-501844 A | 1/2005 |
| WO | 2019/126108 A1 | 6/2019 |

OTHER PUBLICATIONS

Donnelly (Physical Compatibility and Chemical Stability of Ketamine-Morphine Mixtures in Polypropylene Syringes, CJHP, vol. 62, No. 1, Jan.-Feb. 2009) (Year: 2009).*
Jonkman et al. (Ketamine for pain, Sep. 20, 2017, F1000Research, 6(F1000 Faculty Rev): 1711) (Year: 2017).*
Basicmedical Key (Drug stability, Aug. 14, 2016) (Year: 2016).*
"KETALAR—ketamine hydrochloride injection", JHP Pharmaceuticals LLC, Mar. 2012, 6 Pages.
Hashimoto, "Ketamine: a rapid-onset and sustained antidepressant without risk of brain toxicity", Psychological Medicine, vol. 46, Jun. 10, 2016 , pp. 2449-2451.
Huvelle et al., "Long-term stability of ketamine hydrochloride 50 mg/ml injection in 3 ml syringes", Annales Pharmaceutiques Françaises, vol. 74, Apr. 20, 2016, pp. 283-287.
Miolo et al., "A Study on Photostability of Amphetamines and Ketamine in Hair Irradiated under Artificial Sunlight", Brain Sci., May 28, 2018, vol. 8, 96, pp. 1-12.
Berge et al., "Pharmaceutical Salts", Journal of Pharmaceutical Sciences, 1977, vol. 66, No. 1, pp. 1-19.
Daouphars et al., "Physicochemical Stability of Oxycodone-Ketamine Solutions in Polypropylene Syringe and Polyvinyl Chloride Bag for Patient-Controlled Analgesia Use", European Journal of Hospital Pharmacy, Oct. 2016, vol. 25, No. 4, pp. 214-217.
Donnelly, "Physical Compatibility and Chemical Stability of Ketamine-Morphine Mixtures in Polypropylene Syringes", Can J Hosp Pharm., Jan. 2009, vol. 62, No. 1, pp. 28-33.
Fakhri et al., "Antimicrobial, Antioxidant and Cytotoxic Effect of Molybdenum Trioxide Nanoparticles and Application of This for Degradation of Ketamine under Different Light Illumination", Journal of Photochemistry and Photobiology, B: Biology, 2016, vol. 159, pp. 211-217.
Ghaibi et al., "Light-Sensitive Injectable Prescription Drugs", Hospital Pharmacy., vol. 49, No. 2, Feb. 1, 2014, pp. 136-163.
Lin et al., "Photocatalytic Degradation of Morphine, Methamphetamine, and Ketamine by Illuminated TiO2 and ZnO", Reaction Kinetics, Mechanisms and Catalysis, 2013, vol. 110, No. 2, pp. 559-574.
Ou et al., "Photocatalytic Reaction by Fe(III) citrate Complex and its Effect on the Photodegradation of Atrazine in Aqueous Solution", Journal of Photochemistry and Photobiology A: Chemistry, Jun. 2008, vol. 197, Issues 2-3, pp. 382-388.
Paulekuhn, "Trends in Active Pharmaceutical ingredient Salt Selection based on Analysis of the Orange Book Database", J. Med. Chem., 2007, vol. 50, pp. 6665-6672.

(Continued)

*Primary Examiner* — Sahana S Kaup
*Assistant Examiner* — Abdulrahman Abbas
(74) *Attorney, Agent, or Firm* — BakerHostetler

(57) ABSTRACT

The disclosure is directed to pharmaceutical compositions comprising esketamine or a pharmaceutically acceptable salt thereof and an oxidative degradant. In certain aspects, the oxidative degradant is 6-(2-chlorophenyl)-6-oxohexanoic acid or a pharmaceutically acceptable salt thereof. Methods for limiting the formation of oxidative degradants in a pharmaceutical composition comprising esketamine or a pharmaceutically acceptable salt thereof are also disclosed.

15 Claims, 7 Drawing Sheets

(56) References Cited

OTHER PUBLICATIONS

STN Registry, Registry No. 898792-61-5, Chemical Library, 2-chloro-e-oxo-benzenehexanoic acid, Aug. 4, 2006, 1 page.
Unknown, "Spravato Fda Label: Highlights of Prescribing Information", Spravato Fda Label: Highlights of Prescribing Information, May 3, 2019, pp. 1-41.

* cited by examiner

FIG. 4A Batch 5 (average)
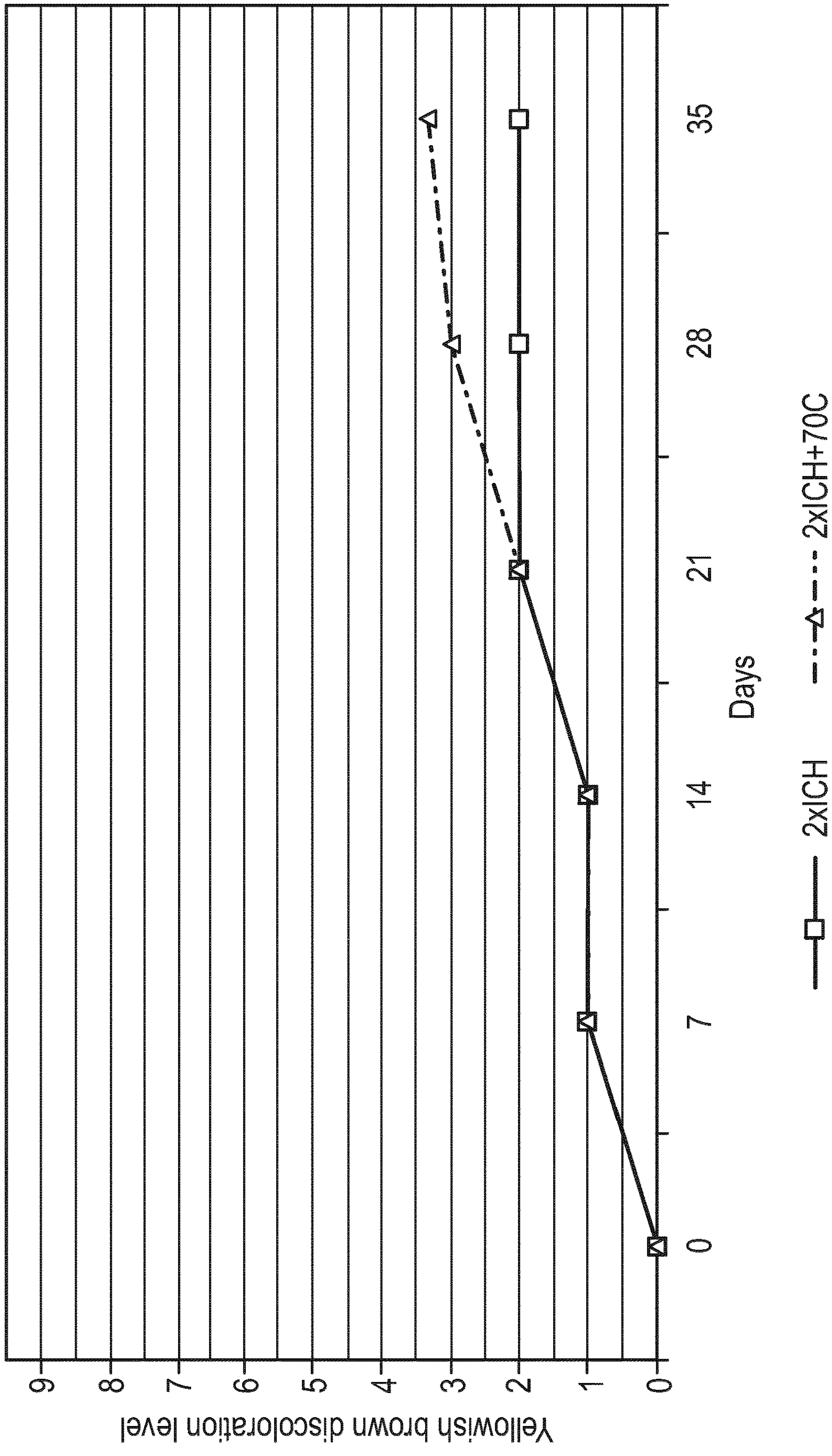

FIG. 4B Batch 1 (average)
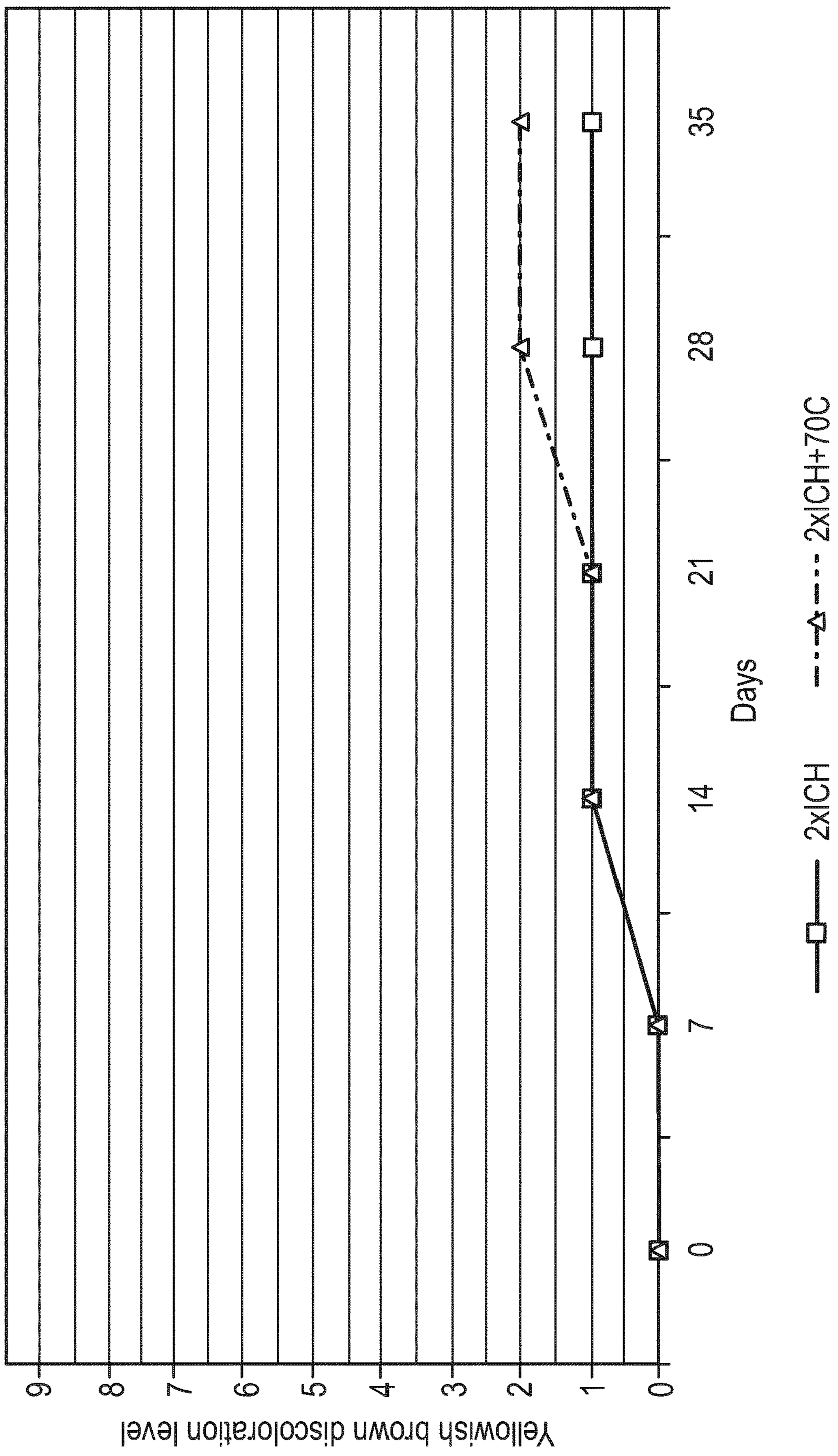

FIG. 5 Vial orientation
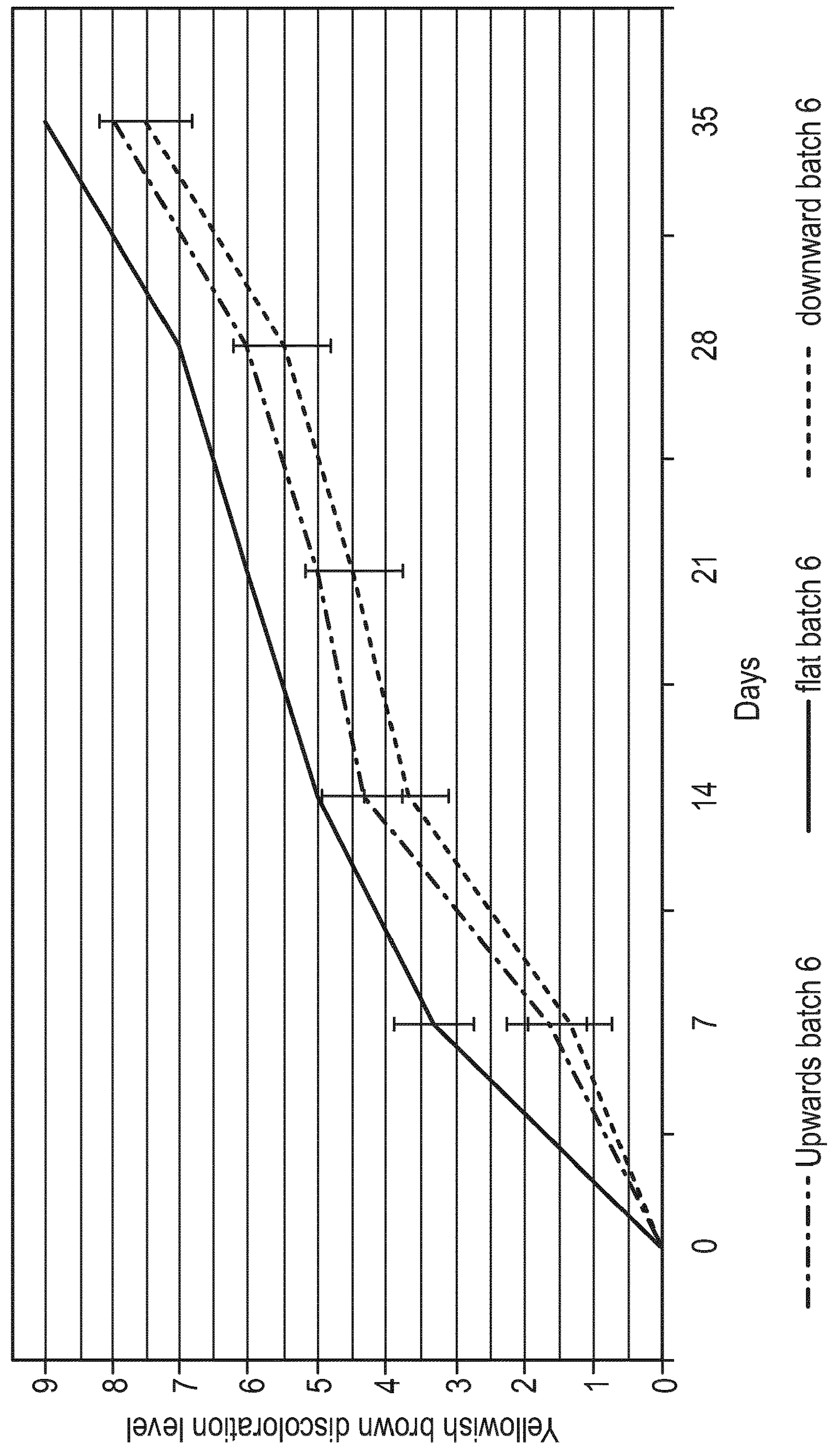

FIG. 5(contd.) Vial with and without stopper
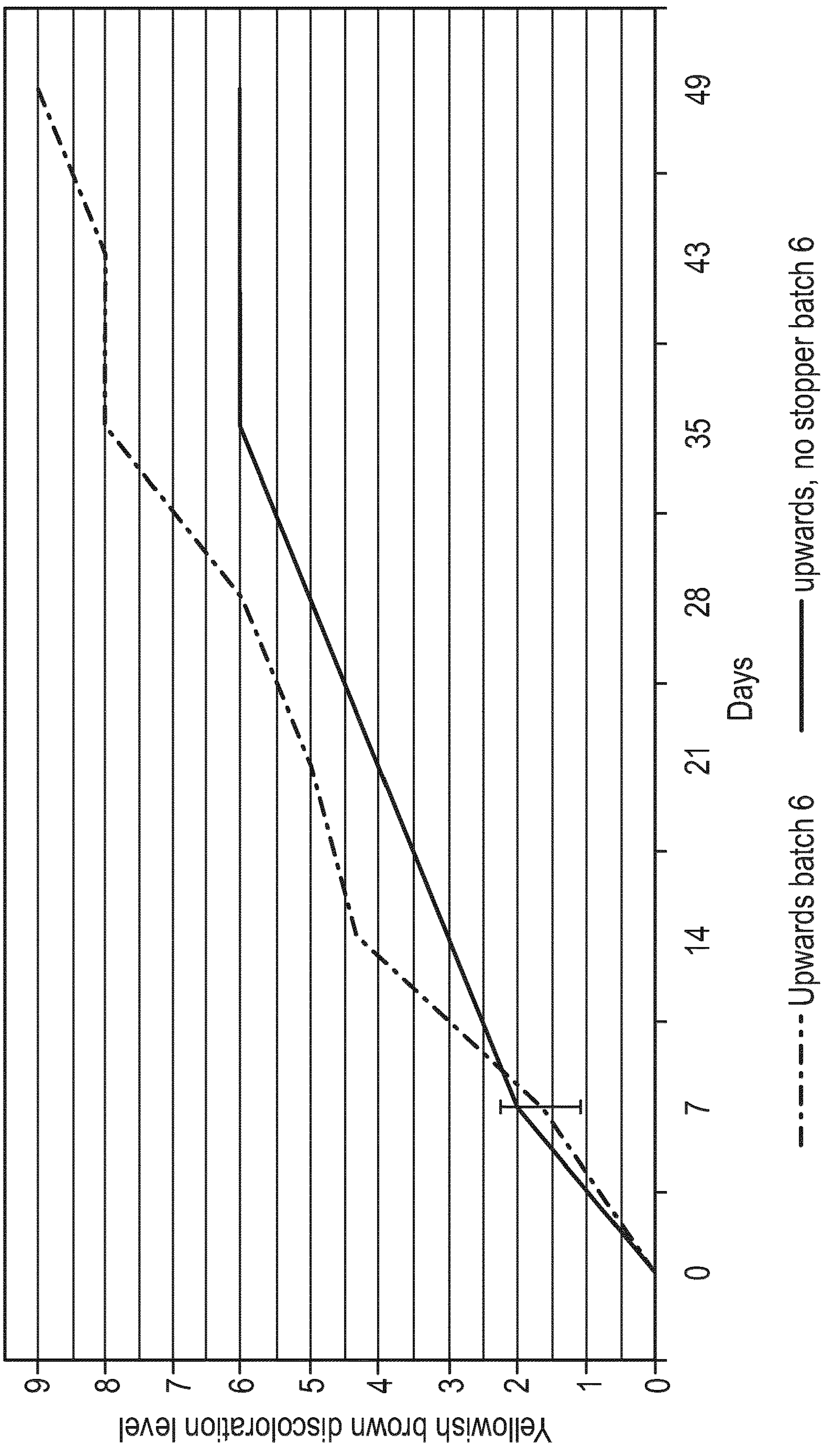

ESKETAMINE FORMULATIONS AND METHODS FOR PREPARATION AND STORAGE

CROSS-REFERENCE TO RELATED APPLICATIONS

This application is the National Stage Application of International Patent Application No. PCT/EP2020/086039, filed Dec. 14, 2020, which claims the priority of U.S. Provisional Patent Application No. 62/947,387, filed Dec. 12, 2019, the disclosures of which are incorporated by reference herein.

TECHNICAL FIELD

This invention is related to pharmaceutical compositions comprising esketamine and methods of preparing and storing the same.

BACKGROUND

Major depressive disorder (MDD) affects about 7-15% of the general population. MDD is associated with significant morbidity and mortality and the leading cause of disability worldwide. About one third of patients fail to achieve remission despite treatment with multiple antidepressant medications, and are considered to have treatment resistant depression (TRD). Such patients who do benefit with oral antidepressants have high rates of relapse even with continuation of treatment.

The impact of TRD on patient's lives is difficult to adequately describe. Many patients have depressive episodes lasting years. Severely depressed patients lose the will to carry on with their lives, there is a 7-fold increase in suicide attempts. Life expectancy is lowered by 10 years. In extreme cases they cannot even engage in basic self-care activities such as bathing or eating, or taking care of themselves, leave alone those in their care as a parent, spouse etc. This impacts not only the patient themselves, but also the family and those dependent on them. They also lose the ability to experience pleasure in doing the things that they used to enjoy, which robs people of the essence of life and what drives it. In effect their lives are taken away from them by TRD.

Pharmaceutical compositions containing esketamine are now approved for the treatment of TRD. Such compositions are designed for administration to a human and, thereby, require precise amounts of esketamine to ensure safe and effective treatment. As such, there remains a need to ensure that such precise esketamine amounts are maintained during and after formulation, with limitations on impurities and/or degradation products.

SUMMARY

In some embodiments, the disclosure provides pharmaceutical compositions comprising esketamine or a pharmaceutically acceptable salt thereof and an oxidative degradant. In certain aspects, the oxidative degradant is 6-(2-chlorophenyl)-6-oxohexanoic acid or a pharmaceutically acceptable salt thereof. In other aspects, the pharmaceutical composition comprises (i) not more than 0.2% (HPLC area) of 6-(2-chlorophenyl)-6-oxohexanoic acid or a pharmaceutically acceptable salt thereof, relative to the amount of esketamine, (ii) not more than 0.2% w/w of 6-(2-chlorophenyl)-6-oxohexanoic acid or a pharmaceutically acceptable salt thereof, relative to the weight of esketamine, or (iii) not more than about 120 ppm of 6-(2-chlorophenyl)-6-oxohexanoic acid or a pharmaceutically acceptable salt thereof. In some embodiments, where the esketamine is in the form of a salt e.g. a salt of the (S)-enantiomer of ketamine, and the amount of an oxidative degradant, in particular 6-(2-chlorophenyl)-6-oxohexanoic acid is defined relative to the amount of esketamine, it is intended that this be interpreted as referring to the amount of the oxidative degradant relative to the total amount of the salt of the (S)-enantiomer of ketamine on an absolute basis (i.e. the amount of degradant relative to the total amount of the salt of the (S)-enantiomer of ketamine).

In other embodiments, the disclosure provides methods for preventing the formation of oxidative degradants in a pharmaceutical composition comprising esketamine or a pharmaceutically acceptable salt thereof, comprising one or more of preparing the pharmaceutical composition in the absence of light; storing the pharmaceutical composition in the absence of light; exposing the pharmaceutical composition to about 6 hours or less of light; or filling a container with the pharmaceutical composition in the absence of light. In some embodiments, the pharmaceutical composition is exposed to about 6 hours or less of light during the combined preparation and storage period of the composition. More preferably, the pharmaceutical composition is exposed to about 1 hour or less of light, even more preferably less than about 30 minutes of light, during the combined preparation and storage period of the composition.

In further embodiments, the disclosure provides processes for preparing a pharmaceutical composition comprising esketamine or a pharmaceutically acceptable salt thereof and (i) not more than 0.2% (HPLC area) of 6-(2-chlorophenyl)-6-oxohexanoic acid or a pharmaceutically acceptable salt thereof, relative to the amount of esketamine, (ii) not more than 0.2% w/w of 6-(2-chlorophenyl)-6-oxohexanoic acid or a pharmaceutically acceptable salt thereof, relative to the weight of esketamine, or (iii) not more than about 120 ppm of 6-(2-chlorophenyl)-6-oxohexanoic acid or a pharmaceutically acceptable salt thereof, comprising mixing the esketamine or a pharmaceutically acceptable salt thereof with one or more pharmaceutically acceptable excipients; and exposing esketamine to about 6 hours or less of light.

BRIEF DESCRIPTION OF THE DRAWINGS

FIG. 4 depicts line graphs comparing color change in vials with stopper of batch 5 (top) and 1 (bottom), exposed to 2×ICH light and followed by storage in the dark at room temperature or 70° C.

FIG. 5 depicts line graphs showing the differences between vial orientations for batch 6 (top) and a comparison of the vials from the same esketamine hydrochloride batch with stopper and without stopper (both with upwards orientation) (bottom).

DETAILED DESCRIPTION OF ILLUSTRATIVE EMBODIMENTS

Figure 1:
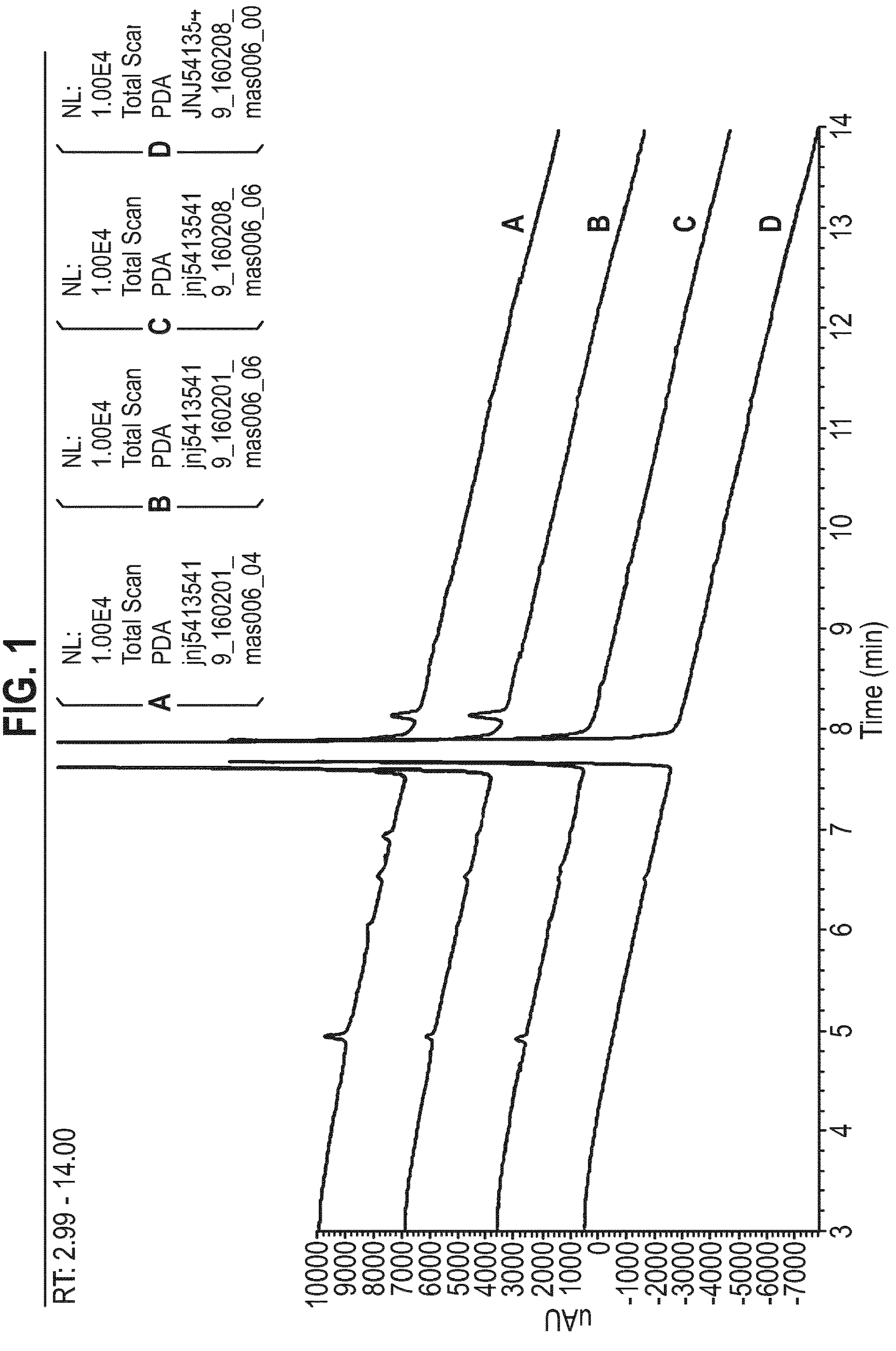
FIG. 1 are overlaid total wavelength chromatograms (210-500 nm; μAU vs. time) showing the result of the light/thermal stress (A) and thermal stress (B) samples compared to discolored (C) and not discolored vials from the same batch (batch 1) (D).

Some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

In their attempts to provide esketamine formulations free from impurities, the inventors found that solutions comprising esketamine were subject to degradation under certain conditions. In some embodiments, esketamine solutions developed color changes, solid material, and/or generated previously unappreciated side-products. Such changes have now been determined to be degradation products, among others. Thus, the present disclosure addresses the identification of these degradation products and need for products containing amounts of the same acceptable to administration to a patient.

As used herein, unless otherwise noted, the term "esketamine" shall mean the (S)-enantiomer of ketamine, i.e., a compound of formula (I):

(I)

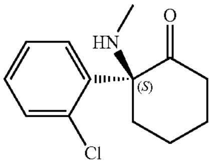

also known as (S)-2-(2-chlorophenyl)-2-(methylamino)cyclohexanone. "Esketamine" shall also mean a salt, e.g., a chloride salt such as the hydrochloride salt, of the (S)-enantiomer of ketamine, i.e., a compound of formula (II):

(II)

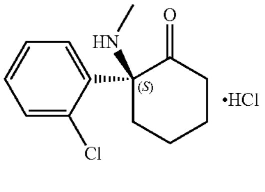

also known as (S)-2-(2-chlorophenyl)-2-(methylamino)cyclohexanone hydrochloride. Preferably, the esketamine is in the form of (S)-2-(2-chlorophenyl)-2-(methylamino)cyclohexanone hydrochloride.

In some embodiments, the esketamine is substantially free of the (R)-enantiomer of ketamine, i.e., a compound of formula (III):

(III)

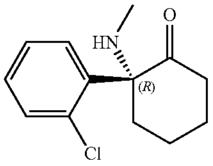

In other embodiments, the esketamine contains less than about 10% by weight, based on the weight of the esketamine sample, of the (R)-enantiomer of ketamine. In further embodiments, the esketamine contains less than about 10%, about 9%, about 8%, about 7%, about 6%, about 5%, about 4%, about 3%, about 2%, about 1%, about 0.5%, about 0.1%, about 0.005%, or about 0.001% by weight, based on the weight of the esketamine sample, of the (R)-enantiomer of ketamine. In yet other embodiments, the esketamine contains about 0.001 to about 10% by weight, based on the weight of the esketamine sample, of the (R)-enantiomer of ketamine. In still further embodiments, the esketamine contains about 0.001 to about 10%, about 0.001 to about 5%, about 0.001 to about 1%, about 0.001 to about 0.5%, about 0.001 to about 0.1%, about 0.1 to about 5%, about 0.1 to about 1%, about 0.1 to about 5%, or about 0.5 to about 5% by weight, based on the weight of the esketamine sample, of the (R)-enantiomer of ketamine. Preferably, the pharmaceutical composition contains less than about 10% by weight, more preferably less than about 1% and even more preferably less than about 0.1% of the (R)-enantiomer of ketamine, based on the total weight of the (S)-enantiomer of ketamine in the pharmaceutical composition.

The term "esketamine" may also include other pharmaceutically acceptable salts thereof, which may readily be selected by those skilled in the art. A "pharmaceutically acceptable salt" is intended to mean a salt of esketamine that is non-toxic, biologically tolerable, or otherwise biologically suitable for administration to the subject. See, generally, G. S. Paulekuhn, "Trends in Active Pharmaceutical Ingredient Salt Selection based on Analysis of the Orange Book Database,", J. Med. Chem., 2007, 50:6665-72, S. M. Berge, "Pharmaceutical Salts", J Pharm Sci., 1977, 66:1-19, and Handbook of Pharmaceutical Salts, Properties, Selection, and Use, Stahl and Wermuth, Eds., Wiley-VCH and VHCA, Zurich, 2002. Examples of pharmaceutically acceptable salts are those that are pharmacologically effective and suitable for administration to patients without undue toxicity, irritation, or allergic response.

Examples of other pharmaceutically acceptable salts include sulfates, pyrosulfates, bisulfates, sulfites, bisulfites, phosphates, monohydrogen-phosphates, dihydrogenphosphates, metaphosphates, pyrophosphates, bromides (such as hydrobromides), iodides (such as hydroiodides), acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, 7-hydroxybutyrates, glycolates, tartrates, methane-sulfonates, propane-sulfonates, naphthalene-1-sulfonates, naphthalene-2-sulfonates, and mandelates. In particular, the salt of esketamine is a hydrochloride salt.

Esketamine Compositions

The present disclosure provides pharmaceutical compositions comprising esketamine or a pharmaceutically acceptable salt thereof and an oxidative degradant. As used herein, the term "composition" is intended to encompass a product comprising the specified ingredients in the specified amounts, as well as any product which results, directly or indirectly, from combinations of the specified ingredients in the specified amounts.

The term "oxidative degradant" as used herein refers to a compound that forms as a result of esketamine oxidation, thereby leading to esketamine degradation. It is believed that esketamine oxidation is the result of external factors having nothing to do with the components of the composition. Such external factors may include, without limitation, exposure to light such as visible light, ultraviolet light, or combinations thereof. Thus, the oxidative degradant may be a photooxidative degradant. The inventors also found that other external factors, such as oxygen, heat, or the like may aid in accelerating esketamine oxidation. Regardless of the source of the oxidative degradant, the formation of the oxidative degradant may be via an autocatalytic cycle. Thus, preventing or minimizing the exposure of esketamine to such external factors is desirable.

Thus, in some embodiments, the oxidative degradant is 6-(2-chlorophenyl)-6-oxohexanoic acid or a pharmaceutically acceptable salt thereof. In other embodiments, the oxidative degradant is 6-(2-chlorophenyl)-6-oxohexanoic acid. In further embodiments, the oxidative degradant is a salt of 6-(2-chlorophenyl)-6-oxohexanoic acid.

"6-(2-Chlorophenyl)-6-oxohexanoic acid" refers to a compound having the following structure:

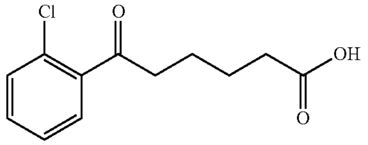 [SMILES: O=C(O)CCCCC(=O)c1ccccc1Cl]

The presence and amount of oxidative degradant present in the pharmaceutical composition may be determined by one skilled in the art. Suitable analytical procedures that may be used to detect oxidative degradants include, without limitation, thin layer chromatography (TLC), liquid chromatography (LC), high performance liquid chromatography (HPLC), mass spectral (MS) analysis, LC-MS; nuclear magnetic resonance spectroscopy (NMR; $^1$H and $^{13}$C), or elemental analysis, or combinations thereof. Preferably, the oxidative degradants are detected and measured using HPLC or LC-MS. As understood to those skilled in the art, HPLC analysis of pharmaceutical compositions results in a spectrum having one peak for each component in the mixture. The ratio of each component is proportional to the ratio of the area of each peak, height of each peak, or combinations thereof. Preferably, the ratio of the components in the pharmaceutical composition is calculated by the peak area. Thus, HPLC is particularly valuable in measuring the purity of any pharmaceutical composition such as pharmaceutical compositions containing esketamine.

In the case of pharmaceutical compositions containing esketamine, the presence and amount of the oxidative degradant may be measured against the amount of esketamine present in the pharmaceutical composition and expressed as a weight percentage.

In other embodiments, the presence and amount of the oxidative degradant may be measured by comparing the LC peaks, such as HPLC peaks, of the esketamine compositions containing the oxidative degradant. Thus, the peak that corresponds to the oxidative degradant is compared with the peak that corresponds to the esketamine present in the pharmaceutical composition and the ratio is calculated. In some embodiments, the pharmaceutical composition comprises esketamine base and the ratio of the area of the HPLC peak corresponding to the oxidative degradant to the area of the HPLC peak corresponding to the esketamine base is calculated. In other embodiments, the pharmaceutical composition comprises an esketamine salt and the ratio of the area of the HPLC peak corresponding to the oxidative degradant to the area of the HPLC peak corresponding to the esketamine salt is calculated. As such, regardless of the form of the esketamine in the pharmaceutical composition, the amount of the oxidative degradant can be calculated using HPLC.

In further embodiments, the amount of the oxidative degradant, no matter how small the amount, may be measured and quantified. Typically, the amounts of the oxidative degradant are measured at parts per million (ppm) levels. Such levels may be measured using traditional techniques known in the art. The levels of the oxidative degradant are calculated on a milligrams per liter basis. Thus, the ppm of oxidative degradant in the pharmaceutical compositions is the mg of the oxidative degradant per liter of the solution, which may be adjusted based on the volume of the pharmaceutical composition.

The esketamine pharmaceutical compositions described herein desirably contain no impurities. However, the ability to maintain an impurity content of 0% in pharmaceutical compositions is often impractical, particularly after storing such compositions for periods of time. Thus, desirably the impurities that are present and/or may form during storage are minimal. In some embodiments, the esketamine pharmaceutical compositions of the disclosure contain not more than (NMT) about 0.2% (HPLC area) of impurities, such as the oxidative degradant, relative to the amount of esketamine. Preferably, the pharmaceutical compositions contain not more than 0.2% (HPLC area) of 6-(2-chlorophenyl)-6-oxohexanoic acid or a pharmaceutically acceptable salt thereof, relative to the amount of esketamine. More preferably, the pharmaceutical compositions contain not more than 0.1% (HPLC area), even more preferably not more than 0.05% (HPLC area) of 6-(2-chlorophenyl)-6-oxohexanoic acid or a pharmaceutically acceptable salt thereof, relative to the amount of esketamine In other embodiments, the pharmaceutical composition contains not more than 0.2% w/w of impurities, such as the oxidative degradant, relative to the weight of esketamine. Preferably, the pharmaceutical composition contain not more than 0.2% w/w of 6-(2-chlorophenyl)-6-oxohexanoic acid or a pharmaceutically acceptable salt thereof, relative to the weight of esketamine. More preferably, the pharmaceutical compositions contain not more than 0.1% w/w, even more preferably not more than 0.05% w/w of 6-(2-chlorophenyl)-6-oxohexanoic acid or a pharmaceutically acceptable salt thereof, relative to the weight of esketamine In further embodiments, the pharmaceutical compositions contain not more than about 120 ppm of impurities, such as the oxidative degradant. Preferably, the pharmaceutical compositions contain not more than about 120 ppm of 6-(2-chlorophenyl)-6-oxohexanoic acid or a pharmaceutically acceptable salt thereof. More preferably, the pharmaceutical compositions contain not more than about 60 ppm, even more preferably not more than about 30 ppm, of 6-(2-chlorophenyl)-6-oxohexanoic acid or a pharmaceutically acceptable salt thereof.

In some embodiments, the pharmaceutical compositions contain not more than about 0.001%, 0.0015%, 0.002%, 0.0025%, 0.003%, 0.0035%, 0.0040%, 0.0045%, 0.0050%, 0.0055%, 0.0060%, 0.0065%, 0.0070%, 0.0075%, 0.0080%, 0.0085%, 0.0090%, 0.0095%, 0.010%, 0.015%, 0.02%, 0.025%, 0.03%, 0.035%, 0.040%, 0.045%, 0.050%, 0.055%, 0.060%, 0.065%, 0.070%, 0.075%, 0.080%, 0.085%, 0.090%, 0.095%, 0.1%, or 0.15% (HPLC area) of the oxidative degradant, relative to the amount of esketamine. In other embodiments, the pharmaceutical compositions contain about 0.001% to about 0.2% (HPLC area) of the oxidative degradant, relative to the amount of esketamine. In further embodiments, the pharmaceutical compositions contain about 0.001% to about 0.2%, 0.0015% to about 0.2%, 0.002% to about 0.2%, 0.0025% to about 0.2%, 0.003% to about 0.2%, 0.0035% to about 0.2%, 0.0040% to about 0.2%, 0.0045% to about 0.2%, 0.0050% to about 0.2%, 0.0055% to about 0.2%, 0.0060% to about 0.2%, 0.0065% to about 0.2%, 0.0070% to about 0.2%, 0.0075% to about 0.2%, 0.0080% to about 0.2%, 0.0085% to about 0.2%, 0.0090% to about 0.2%, 0.0095% to about 0.2%, 0.010% to about 0.2%, 0.015% to about 0.2%, 0.02% to about 0.2%, 0.025% to about 0.2%, 0.03% to about 0.2%, 0.035% to about 0.2%, 0.040% to about 0.2%, 0.045% to about 0.2%, 0.050%, 0.055% to about 0.2%, 0.060% to about 0.2%, 0.065% to about 0.2%, 0.070% to about 0.2%, 0.075% to about 0.2%, 0.080% to about 0.2%, 0.085% to about 0.2%, 0.090% to about 0.2%, 0.095% to about 0.2%, 0.1% to about 0.2%, or 0.15% to about 0.2% (HPLC area) of the oxidative degradant, relative to the amount of esketamine. In still other embodiments, the pharmaceutical compositions contain about 0.001% to about 0.15%, about 0.001% to about 0.1%, about 0.001% to about 0.095%, about 0.001% to about 0.090%, about 0.001% to about 0.085%, about 0.001% to about 0.080%, about 0.001% to about 0.075%, about 0.001% to about 0.070%, about 0.001% to about 0.065%, about 0.001% to about 0.060%, about 0.001% to about 0.055%, about 0.001% to about 0.050%, about 0.001% to about 0.045%, about 0.001% to about 0.040%, about 0.001% to about 0.035%, about 0.001% to about 0.03%, about 0.001% to about 0.025%, about 0.001% to about 0.02%, about 0.001% to about 0.015%, about 0.001% to about 0.010%, about 0.001% to about 0.0095%, about 0.001% to about 0.0090%, about 0.001% to about 0.0085%, about 0.001% to about 0.0080%, about 0.001% to about 0.0075%, about 0.001% to about 0.0070%, about 0.001% to about 0.0065%, about 0.001% to about 0.0060%, about 0.001% to about 0.0055%, about 0.001% to about 0.0050%, about 0.001% to about 0.0045%, about 0.001% to about 0.0040%, about 0.001% to about 0.0035%, about 0.001% to about 0.003%, about 0.001% to about 0.0025%, about 0.001% to about 0.002%, about 0.001% to about 0.0015% (HPLC area) of the oxidative degradant, relative to the amount of esketamine.

In other embodiments, the pharmaceutical compositions contain not more than about 0.001%, 0.0015%, 0.002%, 0.0025%, 0.003%, 0.0035%, 0.0040%, 0.0045%, 0.0050%, 0.0055%, 0.0060%, 0.0065%, 0.0070%, 0.0075%, 0.0080%, 0.0085%, 0.0090%, 0.0095%, 0.010%, 0.015%, 0.02%, 0.025%, 0.03%, 0.035%, 0.040%, 0.045%, 0.050%, 0.055%, 0.060%, 0.065%, 0.070%, 0.075%, 0.080%, 0.085%, 0.090%, 0.095%, 0.1%, or 0.15% w/w of the oxidative degradant, relative to the weight of esketamine. In other embodiments, the pharmaceutical compositions contain about 0.001% to about 0.2% w/w of the oxidative degradant, relative to the weight of esketamine. In further embodiments, the pharmaceutical compositions contain about 0.001% to about 0.2%, 0.0015% to about 0.2%, 0.002% to about 0.2%, 0.0025% to about 0.2%, 0.003% to about 0.2%, 0.0035% to about 0.2%, 0.0040% to about 0.2%, 0.0045% to about 0.2%, 0.0050% to about 0.2%, 0.0055% to about 0.2%, 0.0060% to about 0.2%, 0.0065% to about 0.2%, 0.0070% to about 0.2%, 0.0075% to about 0.2%, 0.0080% to about 0.2%, 0.0085% to about 0.2%, 0.0090% to about 0.2%, 0.0095% to about 0.2%, 0.010% to about 0.2%, 0.015% to about 0.2%, 0.02% to about 0.2%, 0.025% to about 0.2%, 0.03% to about 0.2%, 0.035% to about 0.2%, 0.040% to about 0.2%, 0.045% to about 0.2%, 0.050%, 0.055% to about 0.2%, 0.060% to about 0.2%, 0.065% to about 0.2%, 0.070% to about 0.2%, 0.075% to about 0.2%, 0.080% to about 0.2%, 0.085% to about 0.2%, 0.090% to about 0.2%, 0.095% to about 0.2%, 0.1% to about 0.2%, or 0.15% to about 0.2% w/w of the oxidative degradant, relative to the weight of esketamine. In still other embodiments, the pharmaceutical compositions contain about 0.001% to about 0.15%, about 0.001% to about 0.1%, about 0.001% to about 0.095%, about 0.001% to about 0.090%, about 0.001% to about 0.085%, about 0.001% to about 0.080%, about 0.001% to about 0.075%, about 0.001% to about 0.070%, about 0.001% to about 0.065%, about 0.001% to about 0.060%, about 0.001% to about 0.055%, about 0.001% to about 0.050%, about 0.001% to about 0.045%, about 0.001% to about 0.040%, about 0.001% to about 0.035%, about 0.001% to about 0.03%, about 0.001% to about 0.025%, about 0.001% to about 0.02%, about 0.001% to about 0.015%, about 0.001% to about 0.010%, about 0.001% to about 0.0095%, about 0.001% to about 0.0090%, about 0.001% to about 0.0085%, about 0.001% to about 0.0080%, about 0.001% to about 0.0075%, about 0.001% to about 0.0070%, about 0.001% to about 0.0065%, about 0.001% to about 0.0060%, about 0.001% to about 0.0055%, about 0.001% to about 0.0050%, about 0.001% to about 0.0045%, about 0.001% to about 0.0040%, about 0.001% to about 0.0035%, about 0.001% to about 0.003%, about 0.001% to about 0.0025%, about 0.001% to about 0.002%, or about 0.001% to about 0.0015% w/w of the oxidative degradant, relative to the weight of esketamine.

In further embodiments, the pharmaceutical compositions contain not more than about 120 ppm, about 110 ppm, about 100 ppm, about 90 ppm, about 80 ppm, about 70 ppm, about 60 ppm, about 50 ppm, about 40 ppm, about 30 ppm, about 20 ppm, about 10 ppm, about 5 ppm, or about 1 ppm of impurities, such as the oxidative degradant. In some embodiments, the pharmaceutical compositions contain about 1 to about 120 ppm, about 10 to about 110 ppm, about 10 to about 100 ppm, about 10 to about 90 ppm, about 10 to about 80 ppm, about 10 to about 70 ppm, about 10 to about 60 ppm, about 10 to about 50 ppm, about 10 to about 40 ppm, about 10 to about 30 ppm, or about 10 to about 20 ppm of the oxidative degradant. In other embodiments, the pharmaceutical compositions contain not more than about 5 to about 120 ppm, about 10 to about 120 ppm, about 20 to about 120 ppm, about 30 to about 120 ppm, about 40 to about 120 ppm, about 50 to about 120 ppm, about 60 to about 120 ppm, about 70 to about 120 ppm, about 80 to about 120 ppm, about 90 to about 120 ppm, about 100 to about 120 ppm, or about 110 to about 120 ppm of the oxidative degradant.

The amount of the oxidative impurity present in the solution may also be measured according to the color of the pharmaceutical composition. For example, a visual examination of the pharmaceutical composition may be performed and its color determined. Typically, the yellow hue of the pharmaceutical composition is determined. In some embodiments, a color scale may be utilized to determine the severity of the degradation. For example, a color scale from 1 to 9 may be used, with 1=colorless and 9=yellow/brown. The values therebetween would correspond to escalating yellow intensity such as, e.g., 2=very slightly yellow, 3=slightly yellow, 4=light yellow, 5=yellow, 6=moderately dark yellow, 7=dark yellow, and 8=very dark yellow. The degree of coloration or yellowing of the solution may be determined as descried in the European Pharmacopoeia, 7$^{th}$ edition, Chapter 2, Section 2.2.1, and 2.2.1, pages 21-24, which is hereby incorporated by reference. For example, the degree of coloration may be determined by the following procedure: (i) use tubes of colorless, transparent, neutral glass with a flat base and an internal diameter of 15 mm to 25 mm, (ii) add the solution to be tested to one tube, (iii) add water or a solution lacking esketamine but containing EDTA, citric acid, and water at a pH of 4 to another tube, and (iv) compare the colors of each tube in diffused daylight, viewing vertically against a white background.

The oxidative degradant may form at any time during the preparation or storage of the pharmaceutical composition. In some embodiments, the oxidative degradant forms during preparation of the pharmaceutical compositions. In some embodiments, the oxidative degradant forms during storage of the pharmaceutical compositions. In other embodiments, the oxidative degradant forms during preparation and continues to increase after storage in the absence of light.

As would be understood to those skilled in the art, once prepared, the pharmaceutical compositions may be packaged and optionally stored for periods of time as determined by those skilled in the art. In some embodiments, the pharmaceutical compositions are stored for at least about 1 week. In other embodiments, the pharmaceutical compositions are stored for at least about 1 month, at least about 3 months, at least about 6 months, at least about 12 months, at least about 18 months, or at least about 24 months. However, desirably the pharmaceutical compositions contain (i) not more than 0.2% (HPLC area) of 6-(2-chlorophenyl)-6-oxohexanoic acid or a pharmaceutically acceptable salt thereof, relative to the amount of esketamine, (ii) not more than 0.2% w/w of 6-(2-chlorophenyl)-6-oxohexanoic acid or a pharmaceutically acceptable salt thereof, relative to the weight of esketamine, or (iii) not more than about 120 ppm of 6-(2-chlorophenyl)-6-oxohexanoic acid or a pharmaceutically acceptable salt thereof before, during, and/or after storage. Preferably, at the point at which the pharmaceutical composition is filled into a storage container, it contains (i) not more than 0.2% (HPLC area), more preferably not more than 0.1% (HPLC area), even more preferably not more than 0.05%, (HPLC area) of 6-(2-chlorophenyl)-6-oxohexanoic acid or a pharmaceutically acceptable salt thereof, relative to the amount of esketamine, (ii) not more than 0.2% w/w, more preferably not more than 0.1% w/w, even more preferably not more than 0.05% w/w, of 6-(2-chlorophenyl)-6-oxohexanoic acid or a pharmaceutically acceptable salt thereof, relative to the weight of esketamine, or (iii) not more than about 120 ppm, more preferably not more than about 60 ppm, even more preferably not more than about 30 ppm, of 6-(2-chlorophenyl)-6-oxohexanoic acid or a pharmaceutically acceptable salt thereof.

According to the disclosure, the pharmaceutical compositions are desirably stored or prepared in the absence of light to prevent or minimize oxidative degradation. The term "light" as used herein refers to visible light or light having a wavelength of about 380 nm to about 750 nm. The term "light" may also include light having wavelengths outside of this range. For example, the light may be ultraviolet light.

Storage in the absence of light preferably refers to storage of the pharmaceutical composition in a container having an opacity permitting about 10% or less of light from passing through the container, more preferably permitting about 5% or less of light or even more preferably about less than 1% of light from passing through the container, as measured using an opacimeter. Additionally, it is preferable for the container containing the pharmaceutical composition to be stored in conditions where the ambient light level is less than about 10 lux, more preferably less than about 1 lux, even more preferably less than about 0.1 lux and most preferably less than 0.01 lux.

Exposure to light preferably refers to the exposure of a pharmaceutical composition to light having an intensity of at least 0.1 lux, more preferably at least 1 lux.

Typically, to prevent or minimize oxidative degradation, the exposure time of the pharmaceutical composition to light is limited. In some embodiments, the exposure of the pharmaceutical composition to light is for less than about 1 hour. In some embodiments, the exposure of the pharmaceutical composition to light is for less than about 30 minutes, less than about 25 minutes, less than about 20 minutes, less than about 15 minutes, less than about 10 minutes, less than about 5 minutes, less than about 1 minute, less than about 30 seconds, less than about 15 seconds, or less than about 5 seconds. In other embodiments, the exposure of the pharmaceutical composition to light is for about 1 second to about 1 hour, about 10 seconds to about 1 hour, about 15 seconds to about 1 hour, about 30 seconds to about 1 hour, about 1 minute to about 1 hour, about 5 minutes to about 1 hour, about 10 minutes to about 1 hour, about 15 minutes to about 1 hour, about 20 minutes to about 1 hour, about 25 minutes to about 1 hour, about 30 minutes to about 1 hour, or about 45 minutes to about 1 hour. In further embodiments, the exposure of the pharmaceutical composition to light if for about 1 second to about 45 minutes, about 1 second to about 30 minutes, about 1 second to about 15 minutes, about 1 second to about 10 minutes, about 1 second to about 5 minutes, about 1 second to about 1 minute, about 10 seconds to about 45 minutes, about 10 seconds to about 30 minutes, about 10 seconds to about 15 minutes, about 10 seconds to about 10 minutes, about 10 seconds to about 5 minutes, about 10 seconds to about 1 minute, about 30 seconds to about 45 minutes, about 30 seconds to about 30 minutes, about 30 seconds to about 15 minutes, about 3 seconds to about 10 minutes, about 30 seconds to about 5 minutes, about 30 seconds to about 1 minute, about 1 minute to about 45 minutes, about 1 minute to about 30 minutes, about 1 minute to about 15 minutes, about 1 minute to about 10 minutes, or about 1 minute to about 5 minutes. There may also be zero exposure of the pharmaceutical composition to light during preparation or storage. The exposure of the pharmaceutical composition to light during preparation is preferably less than about 1 hour, more preferably less than about 30 minutes, even more preferably less than about 5 minutes. The exposure of the pharmaceutical composition to light during storage may be less than about 1 hour, more preferably less than about 30 minutes, even more preferably less than about 5 minutes. Preferably, the total exposure of the pharmaceutical composition to light during preparation and storage is less than about 1 hour, more preferably less than about 30 minutes, even more preferably less than about 5 minutes.

In some preferred embodiments, the pharmaceutical compositions desirably contain not more than 0.2% (HPLC area), more preferably not more than 0.1% (HPLC area), of 6-(2-chlorophenyl)-6-oxohexanoic acid or a pharmaceutically acceptable salt thereof, relative to the amount of esketamine, after storage in the absence of light. In other preferred embodiments, the pharmaceutical composition comprises esketamine or a pharmaceutically acceptable salt thereof and not more than 0.2% (HPLC area), more preferably not more than 0.1% (HPLC area) of 6-(2-chlorophenyl)-6-oxohexanoic acid or a pharmaceutically acceptable salt thereof, relative to the amount of esketamine, after storage in the absence of light for at least 6 months. In further preferred embodiments, the pharmaceutical compositions desirably contain not more than 0.2% w/w, more preferably not more than 0.1% w/w, of 6-(2-chlorophenyl)-6-oxohexanoic acid or a pharmaceutically acceptable salt thereof, relative to the weight of esketamine, after storage in the absence of light. In yet other preferred embodiments, the pharmaceutical composition comprises esketamine or a pharmaceutically acceptable salt thereof and not more than 0.2% w/w, more preferably not more than 0.1% w/w, of 6-(2-chlorophenyl)-6-oxohexanoic acid or a pharmaceutically acceptable salt thereof, relative to the weight of esketamine, after storage in the absence of light for at least 6 months. In still further preferred embodiments, the pharmaceutical compositions desirably contain not more than about 120 ppm of 6-(2-chlorophenyl)-6-oxohexanoic acid or a pharmaceutically acceptable salt thereof after storage in the absence of light. In still further preferred embodiments, the pharmaceutical compositions desirably contain not more than about 120 ppm, more preferably not more than about 60 ppm, of 6-(2-chlorophenyl)-6-oxohexanoic acid or a pharmaceutically acceptable salt thereof after storage in the absence of light for at least 6 months. In yet other preferred embodiments, the pharmaceutical composition comprises esketamine or a pharmaceutically acceptable salt thereof and not more than about 120 ppm of 6-(2-chlorophenyl)-6-oxohexanoic acid or a pharmaceutically acceptable salt thereof. Preferably, the pharmaceutical composition is stored at a temperature in the range of about 20° C. to about 75° C. in an atmosphere having a relative humidity of about 25% to about 80%, more preferably at a temperature in the range of about 20° C. to about 30° C. in an atmosphere having a relative humidity of about 25% to about 30%.

The storage of the pharmaceutical composition in the absence of light (for example, by storing the pharmaceutical composition in a substantially opaque container that has an opacity permitting about 10% or less of light from passing through the container as measured using an opacimeter), results in a lower level of oxidative degradants, in particular 6-(2-chlorophenyl)-6-oxohexanoic acid or a pharmaceutically acceptable salt thereof, compared to the same pharmaceutical composition that has not been stored under such conditions. Similarly, the preparation and filling of the pharmaceutical composition into containers in the absence of light (for example, by exposing the pharmaceutical composition to a total of 1 hour or less of light, preferably 30 minutes or less of light, during preparation of the composition and filling of a container with the composition), results in a lower level of oxidative degradants compared to the same pharmaceutical composition which is exposed to more light during the preparation and filling processes.

In a preferred embodiment, the pharmaceutical composition comprises esketamine or a pharmaceutically acceptable salt thereof and not more than 0.2% (HPLC area) or not more than 0.2% w/w of 6-(2-chlorophenyl)-6-oxohexanoic acid or a pharmaceutically acceptable salt thereof, relative to the amount of esketamine, after storage in the absence of light for 6 months. More preferably, the pharmaceutical composition comprises not more than 0.1% (HPLC area) or not more than 0.1% w/w of 6-(2-chlorophenyl)-6-oxohexanoic acid or a pharmaceutically acceptable salt thereof, relative to the amount of esketamine, after storage in the absence of light for 6 months. Preferably, the pharmaceutical composition contains not more than 0.2% (HPLC area) or not more than 0.2% w/w of 6-(2-chlorophenyl)-6-oxohexanoic acid or a pharmaceutically acceptable salt thereof, relative to the amount of esketamine, after storage in the absence of light for 12 months, 18 months or 24 months. More preferably, the pharmaceutical composition comprises not more than 0.1% (HPLC area) or not more than 0.1% w/w of 6-(2-chlorophenyl)-6-oxohexanoic acid or a pharmaceutically acceptable salt thereof, relative to the amount of esketamine, after storage in the absence of light for 12 months, 18 months or 24 months.

Preferably, the pharmaceutical composition is stored in a substantially opaque container. Preferably, the substantially opaque container has an opacity permitting about 10% or less of light from passing through the container as measured using an opacimeter.

The pharmaceutical compositions may be stored at any condition that does not compromise the integrity of the components or the pharmaceutical composition. Thus, the pharmaceutical compositions may be stored at a temperature in the range of about 20° C. to about 75° C. In some embodiments, the pharmaceutical compositions are stored at a temperature in the range of about 20° C. to about 70° C., about 20° C. to about 65° C., about 20° C. to about 60° C., about 20° C. to about 55° C., about 20° C. to about 50° C., about 20° C. to about 45° C., about 20° C. to about 40° C., about 20° C. to about 35° C., about 20° C. to about 30° C., about 25° C. to about 75° C., about 30° C. to about 75° C., about 35° C. to about 75° C., about 40° C. to about 75° C., about 45° C. to about 75° C., about 50° C. to about 75° C., about 55° C. to about 75° C., about 60° C. to about 75° C., or about 65° C. to about 75° C. In other embodiments, the pharmaceutical compositions are stored at a temperature in the range of about 20° C. to about 40° C., about 20° C. to about 35° C., about 20° C. to about 30° C., about 20° C. to about 25° C., about 25° C. to about 40° C., about 25° C. to about 35° C., about 25° C. to about 30° C., or about 30° C. to about 40° C. Preferably, the pharmaceutical compositions are stored at ambient conditions such as room temperature. Preferably, room temperature corresponds to a temperature of about 20° C. to about 30° C.

The pharmaceutical compositions are also desirably stored in a facility at conditions having a relative humidity of less than about 80%. In some embodiments, the pharmaceutical compositions are stored in a facility having a relative humidity of about 25 to about 80%, about 30 to about 80%, about 35 to about 80%, about 40 to about 80%, about 45 to about 80%, about 50 to about 80%, about 55 to about 80%, about 60 to about 80%, about 65 to about 80%, about 70 to about 80%, about 75 to about 80%, about 25 to about 75%, about 25 to about 70%, about 25 to about 65%, about 25 to about 60%, about 25 to about 55%, about 25 to about 50%, about 25 to about 45%, about 25 to about 40%, about 25 to about 35%, or about 25 to about 30%. Preferably, the pharmaceutical composition is stored in a facility at conditions having a relative humidity of about 25 to about 30%.

In order to sustain optimal performance of the pharmaceutical compositions and integrity of the components thereof, the pharmaceutical composition is enclosed or contained in a closed container. The container may be composed of any material that does not react with one or more of the components of the pharmaceutical composition, which may be determined by those skilled in the art. Examples of suitable materials for use as the container include, without limitation, glass, plastic, or metal. Preferably, the closed container is glass, e.g., a glass vial. Desirably, the container is substantially opaque to light as described above. In some embodiments, the container is an amber container.

The term "substantially opaque" as used herein refers to an object that is not transparent, i.e., not permitting the passage of light therethrough. Thus, substantially opaque refers to an object having an opacity permitting about 10% or less of light from passing through the container. Opacity may be measured by those skilled in the art using an opacimeter, desirably using a contrast-ratio-method, by measuring the amount of light reflected from the object. In some embodiments, substantially opaque refers to permitting about 9%, about 8%, about 7%, about 6%, about 5%, about 4%, about 3%, about 2%, about 1%, about 0.5%, about 0.1%, or less, or about 0% of light from transmitted light. Preferably, "substantially opaque" refers to an object having an opacity permitting about 5% or less of light from passing through the container, more preferably having an opacity permitting about 1% or less of light from passing through the container. Thus, substantially opaque refers to an object, such as a container used herein, that reflects about 90% or more of light. In some embodiments, a substantially opaque object, such as a container used herein, reflects about 91%, about 92%, about 93%, about 94%, about 95%, about 96%, about 97%, about 98%, about 99%, or more, or about 100% or of light.

The container containing the esketamine pharmaceutical composition may be sealed or closed using any device suitable for such a purpose. Examples of such devices can include, without limitation, lids, caps, stoppers, or the like. The device is, desirably, composed of a material that does not react or interact with the components of the pharmaceutical composition. Examples of materials that are less suitable for sealing the container include rubber, silicone, or combinations thereof. Preferably, the container and/or the device for sealing or closing the container does not comprise any rubber or silicone. More preferably, the container and/or the device for sealing or closing the container does not contain any silicone. As such, the device for sealing the container may be plastic, glass, or combinations thereof, such as a plastic lid, glass lid, plastic stopper, glass stopper, plastic cap, or glass cap, among others. Preferably, the device is plastic. Alternatively, the container may be sealed using heat, resulting in a sealed glass vial, i.e., an ampule that is optionally scored to permit easy opening.

The closed container containing the esketamine pharmaceutical composition may be placed in a second container, desirably one that is substantially opaque to light. By doing so, this further prevents the likelihood of the esketamine composition from being exposed to light. In some embodiments, the second container is a box, bag, sack, or the like. Suitably, the second container is suitable for transport. The second container may be designed to hold a single container that contains the esketamine composition or is designed to hold several containers of the esketamine composition. In some embodiments, the second container is an amber low-density polyethylene (LDPE) bag, optionally contained within a third container such as carton box or in a zippered aluminum bag.

In some embodiments, the pharmaceutical composition is stored in a substantially opaque closed container, at a temperature of about 20° C. to about 75° C. and a relative humidity of less than 80%, more preferably at a temperature of about 20° C. to about 30° C. and a relative humidity of about 25% to about 30%. Preferably, the substantially opaque container has an opacity permitting about 10% or less of light from passing through the container as measured using an opacimeter.

In some embodiments, the pharmaceutical compositions desirably contain not more than 0.2% (HPLC area) of 6-(2-chlorophenyl)-6-oxohexanoic acid or a pharmaceutically acceptable salt thereof, relative to the amount of esketamine, after storage in the absence of light for 6 months at a temperature of about 20° C. to about 75° C. and a relative humidity of less than 80% in a closed container. Preferably, the closed container has an opacity permitting about 10% or less of light, more preferably 5% or less of light, from passing through the container. More preferably, the pharmaceutical compositions contain not more than 0.2% (HPLC area) of 6-(2-chlorophenyl)-6-oxohexanoic acid or a pharmaceutically acceptable salt thereof after storage under said conditions for 12 months, 18 months or 24 months.

The pharmaceutical compositions also may contain other impurities aside from oxidative degradants. In some embodiments, the pharmaceutical compositions may contain one or more esketamine metabolites such as noresketamine. In other embodiments, the pharmaceutical compositions may contain not more than about 0.2% (HPLC area) of noresketamine or a pharmaceutically acceptable salt thereof, relative to the amount of esketamine.

In the preferred pharmaceutical composition, esketamine free base or an esketamine salt such as esketamine hydrochloride is intimately admixed with a pharmaceutical carrier, preferably water, according to conventional pharmaceutical compounding techniques, which carrier may take a wide variety of forms depending of the form of preparation desired for administration. Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

A suitable aqueous formulation of esketamine comprises water, esketamine, and (i) not more than about 0.2% (HPLC area) of an oxidative degradant or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or a pharmaceutically acceptable salt thereof. In such compositions, esketamine is present in a concentration in the range of from about 100 mg/mL to about 250 mg/mL, or any concentration or range therein, based on the total volume of the pharmaceutical composition. Preferably, esketamine is present in a concentration in the range of from about 125 mg/ml to about 180 mg/mL, or any concentration or range therein. More preferably, esketamine is present in a concentration in the range of from about 140 mg/mL to about 160 mg/mL, or any concentration or range therein, for example, in a concentration of about 140 mg/mL. The concentrations refer to an esketamine base equivalent concentration.

Suitable pharmaceutical compositions for use herein are preferably an aqueous formulation. As used herein, unless otherwise noted, the term "aqueous" shall mean that the primary liquid component of the formulation is water. Preferably, water constitutes greater than about 80 wt % of the liquid component of the pharmaceutical composition, more preferably greater than about 90 wt %, more preferably greater than about 95 wt %, more preferably about 98 wt %. In suitable pharmaceutical compositions for use herein, the water content of the composition is within the range of 85±14 wt. %, more preferably 85±12 wt. %, still more preferably 85±10 wt. %, most preferably 85±7.5 wt. % and in particular 85±5 wt. %, based on the total weight of the composition. In other pharmaceutical compositions for use herein, preferably the water content of the composition is within the range of 90±14 wt. %, more preferably 90±12 wt. %, still more preferably 90±10 wt. %, most preferably 80±7.5 wt.-% and in particular 90±5 wt. %, based on the total weight of the composition. In further pharmaceutical compositions for use herein, the water content of the composition is within the range of 95±4.75 wt. %, more preferably 95±4.5 wt. %, still more preferably 95±4 wt. %, yet more preferably 95±3.5 wt. %, most preferably 95±3 wt.-% and in particular 95±2.5 wt. %, based on the total weight of the composition. In still other pharmaceutical compositions for use herein, the water content of the composition is within the range of from 75 to 99.99 wt. %, more preferably 80 to 99.98 wt. %, still more preferably 85 to 99.95 wt. %, yet more preferably 90 to 99.9 wt. %, most preferably 95 to 99.7 wt. % and in particular 96.5 to 99.5 wt. %, based on the total weight of the composition.

In a preferred embodiment, the aqueous formulations desirably contain not more than 0.2% (HPLC area) of 6-(2-chlorophenyl)-6-oxohexanoic acid or a pharmaceutically acceptable salt thereof, relative to the amount of esketamine, after storage in the absence of light for 6 months at a temperature of about 20° C. to about 75° C. and a relative humidity of less than 80% in a closed container. Preferably, the closed container has an opacity permitting about 10% or less of light, more preferably 5% or less of light, from passing through the container. More preferably, the aqueous formulations contain not more than 0.2% (HPLC area) of 6-(2-chlorophenyl)-6-oxohexanoic acid or a pharmaceutically acceptable salt thereof after storage under said conditions for 12 months, 18 months or 24 months.

In other pharmaceutical compositions for use herein, the composition further comprises one or more buffers and/or buffer systems (i.e. conjugate acid-base-pairs). As used herein, the term "buffer" shall mean any solid or liquid composition (preferably an aqueous, liquid composition) which when added to an aqueous formulation adjusts the pH of said formulation. One skilled in the art will recognize that a buffer may adjust the pH of the aqueous formulation in any direction (toward more acidic, more basic or more neutral pH). Preferably, the buffer is pharmaceutically acceptable. Suitable examples of buffers which may be used in the aqueous formulations include, but are not limited to sodium hydroxide (NaOH), citric acid, sodium dihydrogen phosphate, disodium hydrogen phosphate, acetic acid, boric acid, sodium borate, succinic acid, tartaric acid, malic acid, lactic acid, furmaric acid, and the like. Preferably, the buffer or buffer system is selected from the group consisting of NaOH, citric acid, sodium dihydrogen phosphate and disodium hydrogen phosphate. In an embodiment, the buffer is selected to adjust the pH of the esketamine pharmaceutical compositions (e.g. the aqueous formulations described herein) into a pH in the range of from about pH 3.5 to about pH 6.5, or any amount or range therein. Preferably, the buffer is selected to adjust the pH of the esketamine compositions to about in the range of from about pH 4.0 to about pH 5.5, or any amount or range therein, more preferably, in the range of from about pH 4.5 to about pH 5.0, or any amount or range therein. Preferably, the concentration of the buffer and buffer system, respectively, preferably NaOH, is adjusted to provide a sufficient buffer capacity.

In some embodiments, the disclosure is directed to a pharmaceutical composition comprising esketamine, water, a buffer or buffer system, preferably NaOH, and (i) not more than about 0.2% (HPLC area) of an oxidative degradant or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof. In such compositions, the buffer or buffer system is present in an amount sufficient to yield a formulation with a pH in the range of from about pH 4.0 to about pH 6.0, or any amount or range therein. In other embodiments, the disclosure is directed to pharmaceutical compositions containing one or more of citric acid monohydrate, edetate disodium, sodium hydroxide, and water, and (i) not more than about 0.2% (HPLC area) of oxidative degradants, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof.

Optionally the pharmaceutical compositions may contain a preservative. As used herein, unless otherwise noted, the terms "antimicrobial preservative" and "preservative" refer to any substance that is usually added to pharmaceutical compositions in order to preserve them against microbial degradation or microbial growth. In this regard, microbial growth typically plays an essential role, i.e., the preservative serves the main purpose of avoiding microbial contamination. In one aspect, it may also be desirable to avoid any effect of the microbes on the active ingredients and excipients, respectively, i.e. to avoid microbial degradation. Representative examples of preservatives include, but are not limited to, benzalkonium chloride, benzethonium chloride, benzoic acid, sodium benzoate, benzyl alcohol, bronopol, cetrimide, cetylpyridinium chloride, chlorhexidine, chlorbutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, sodium propionate, thimerosal, methyl paraben, ethyl paraben, propyl paraben, butyl paraben, isobutyl paraben, benzyl paraben, sorbic acid, and potassium sorbate.

The complete absence of preservatives in the pharmaceutical compositions used herein is preferred when the content of esketamine is sufficiently high so that due to its preservative property the desired shelf life or in use stability can be achieved by the presence of the drug itself. Preferably, under these circumstances the concentration of esketamine is at least 120 mg/mL, preferably in the range of from about 120 mg/mL to about 175 mg/ml, or any concentration or range therein, more preferably in concentration in the range of from about 125 mg/mL to about 150 mg/mL, or any concentration or range therein, for example at about 126 mg/mL or at about 140 mg/mL. The concentrations refer to an esketamine base equivalent concentration.

As used herein, the terms "penetration agent", "penetration enhancer", and "penetrant" refer to any substance that increases or facilitates absorption and/or bioavailability of the active ingredient (e.g. esketamine) of a pharmaceutical composition. Preferably, the penetration agents increases or facilitates absorption and/or bioavailability of the active ingredient (e.g. esketamine) of a pharmaceutical composition, following nasal administration (i.e. increases or facilitates absorption and/or bioavailability of the active ingredient through the mucosal membrane). Suitable examples include, but are not limited to tetradecyl maltoside, sodium glycocholate, tauroursodeoxycholic acid (TUDCA), lecithines, and the like; and chitosan (and salts), and surface active ingredients such as benzalkonium chloride, sodium dodecyl sulfate, sodium docusate, polysorbates, laureth-9, oxtoxynol, sodium deoxycholate, polyarginine, and the like. Preferably, the penetration agent is tauroursodeoxycholic acid (TUDCA). The penetration agent may work via any mechanism, including for example by increasing the membrane fluidity, creating transient hydrophilic pores in the epithelial cells, decreasing the viscosity of the mucus layer or opening up tight junctions. Some penetration agents (for example bile salts and fusidic acid derivatives) may also inhibit the enzymatic activity in the membrane, thereby improving bioavailability of the active ingredient. Preferably, the penetration agent is selected to meet one or more, more preferably all, of the following general requirements:

(a) It is effective at increasing absorption (preferably nasal absorption) of the active ingredient, preferably in a temporary and/or reversible manner;
(b) It is pharmacologically inert;
(c) It is non-allergic, non-toxic and/or non-irritating;
(d) It is highly potent (effective in small amounts);
(e) It is compatible with the other components of the pharmaceutical composition;
(f) It is odorless, colorless and/or tasteless;
(g) It is accepted by regulatory agencies; and
(h) It is inexpensive and available in high purity.

In one embodiment, the penetration agent is selected to increase penetration (absorption and/or bioavailability of esketamine) without nasal irritation. In another embodiment, the penetration agent is selected to improve absorption and/or bioavailability of esketamine; and further selected to enhance uniform dosing efficacy.

In an embodiment, the disclosure is directed to a pharmaceutical composition comprising esketamine, water, and (i) not more than about 0.2% (HPLC area) of an oxidative degradant or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof, wherein the pharmaceutical composition does not contain an antimicrobial preservative; and wherein the pharmaceutical compositions further contains a penetration enhancer, preferably TUDCA.

In another embodiment, the disclosure is directed to a pharmaceutical composition comprising esketamine, water, and (i) not more than about 0.2% (HPLC area) of an oxidative degradant or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof, wherein the pharmaceutical composition does not contain an antimicrobial preservative; and wherein the pharmaceutical compositions further contains tauroursodeoxycholic acid (TUDCA); wherein the TUDCA is present in a concentration in the range of from about 1.0 mg/mL to about 25.0 mg/mL, or any range therein, preferably in a concentration in the range of from about 2.5 mg/mL to about 15 mg/mL, or any range therein, preferably in a concentration in the range of from about 5 mg/mL to about 10 mg/mL, or any range therein. In another embodiment, the disclosure is directed to pharmaceutical composition wherein the TUDCA is present at a concentration of about 5 mg/mL. In another embodiment, the disclosure is directed to pharmaceutical composition wherein the TUDCA is present at a concentration of about 10 mg/mL. See, e.g., the pharmaceutical compositions disclosed in U.S. Patent Application Publication No. US-2019/0117591, which is incorporated herein by reference.

The pharmaceutical compositions for use herein may further contain one or more additional excipients, for example, wetting agents, surfactant components, solubilizing agents, thickening agents, colorant agents, antioxidant components, and the like.

Examples of a suitable antioxidant component, if used, include, but are not limited to one or more of the following: sulfites; ascorbic acid; ascorbates, such as sodium ascorbate, calcium ascorbate, or potassium ascorbate; ascorbyl palmitate; fumaric acid; ethylene diamine tetraacetic acid (EDTA) or its sodium or calcium salts; tocopherol; gallates, such as propyl gallate, octyl gallate, or dodecyl gallate; vitamin E; and mixtures thereof. The antioxidant component provides long term stability to the liquid compositions. Addition of the antioxidant component can help enhance and ensure the stability of the compositions and renders the compositions stable even after six months at 40° C. A suitable amount of the antioxidant component, if present, is about 0.01 wt. % to about 3 wt. %, preferably about 0.05 wt. % to about 2 wt. %, of the total weight of the composition.

Solubilizing and emulsifying agents can be included to facilitate more uniform dispersion of the active ingredient or other excipient that is not generally soluble in the liquid carrier. Examples of a suitable emulsifying agent, if used, include, but are not limited to, for example, gelatin, cholesterol, acacia, tragacanth, pectin, methyl cellulose, carbomer, and mixtures thereof. Examples of a suitable solubilizing agent include polyethylene glycol, glycerin, D-mannitol, trehalose, benzyl benzoate, ethanol, trisaminomethane, cholesterol, triethanolamine, sodium carbonate, sodium citrate, sodium salicylate, sodium acetate, and mixtures thereof.

Preferably, the solubilizing agent includes glycerin. The solubilizing or emulsifying agent is/are generally present in an amount sufficient to dissolve or disperse the active ingredient, i.e., esketamine, in the carrier. Typical amounts when a solubilizing or an emulsifier are included are from about 1 wt. % to about 80 wt. %, preferably about 20 wt. % to about 65 wt. %, and more preferably about 25 wt. % to about 55 wt. %, of the total weight of the composition.

A suitable isotonizing agent, if used, includes sodium chloride, glycerin, D-mannitol, D-sorbitol, glucose, and mixtures thereof. A suitable amount of the isotonizing agent, when included, is typically about 0.01 wt. % to about 15 wt. %, more preferably about 0.3 wt. % to about 4 wt. %, and more preferably about 0.5 wt. % to about 3 wt. %, of the total weight of the composition.

A suspending agent or viscosity increasing agent can be added to the pharmaceutical compositions, to for example, increase the residence time in the nose. Suitably examples include, but are not limited to, hydroxypropyl methylcellulose, sodium carmellose, microcrystalline cellulose, carbomer, pectin, sodium alginate, chitosan salts, gellan gum, poloxamer, polyvinyl pyrrolidone, xanthan gum, and the like.

Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Preparation Methods

The formation of oxidative degradants can be reduced or eliminated by taking appropriate measures when preparing the pharmaceutical composition, filling containers with the pharmaceutical compositions, packaging the containers containing the pharmaceutical compositions, storing the pharmaceutical compositions, handling of the pharmaceutical compositions by the patient prior to administration, or combinations thereof.

In some embodiments, the disclosure provides methods for reducing or preventing the formation of oxidative degradants when preparing pharmaceutical compositions comprising esketamine. In doing so, exposure of pharmaceutical compositions containing esketamine are minimized. In some embodiments, the pharmaceutical compositions are prepared in the absence of light as described herein. One or more of the steps during the preparation may be modified to reduce or eliminate the amount of light that comes into contact with one or more of the components of the esketamine compositions. Reaction steps include mixing steps, transferring steps, filtering steps, or purification steps, or any combination thereof. Desirably, the pharmaceutical composition comprising esketamine or a pharmaceutically acceptable salt thereof and (i) not more than 0.2% (HPLC area) of 6-(2-chlorophenyl)-6-oxohexanoic acid or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof, is prepared by mixing esketamine or a pharmaceutically acceptable salt thereof with one or more pharmaceutically acceptable excipients; and exposing esketamine to about 6 hours or less of light. More preferably, the esketamine is exposed to about 1 hour or less of light during preparation of the composition, even more preferably about 30 minutes or less of light. Techniques known to those skilled in the art to avoid or minimize the presence of light during the preparation may be applied including, without limitation, using opaque equipment covers, metal or ceramic vessels instead of glass vessels, or combinations thereof. For example, the mixing may be performed using a mixing substrate that is substantially opaque to light, such as a light protective foil. However, it is particularly desirable to minimize light exposure to the esketamine pharmaceutical compositions immediately after its preparation. Thus, it is contemplated that exposure of the esketamine pharmaceutical composition be monitored from its point of preparation to its final packaging step. Desirably, the monitoring is performed on a continuous basis, but modifications to such monitoring may be made by one skilled in the art. Records can be taken to ensure proper measurement of light exposure. In a preferred embodiment, the preparation of the pharmaceutical composition comprises mixing esketamine or a pharmaceutically acceptable salt thereof with one or more pharmaceutically acceptable excipients in a vessel surrounded by a light protective foil, or a vessel that is protected by opaque equipment covers. In another preferred embodiment, the mixing may take place in a metal or ceramic vessel. It is preferable for the ambient light level during preparation of the composition to be less than about 10 lux, more preferably less than about 1 lux, even more preferably less than about 0.1 lux and most preferably less than about 0.01 lux. More preferably, the ambient light level during preparation of the composition is less than about 10 lux, even more preferably less than about 1 lux or less than about 0.1 lux or less than about 0.01 lux, and the vessel in which the esketamine or a pharmaceutically acceptable salt thereof is mixed with one or more pharmaceutically acceptable excipients is protected from exposure to light, for example by surrounding the vessel with a light protective foil or protecting the vessel using opaque equipment covers.

In other embodiments, the disclosure provides methods for reducing or preventing the formation of oxidative degradants when filling containers with the pharmaceutical compositions. Thus, the containers are filled with the pharmaceutical compositions in the absence of light. The containers are filled using equipment such as a funnel, manifold, or the like. Light blocking techniques may be used and include, without limitation, using opaque shields that cover the filling station, opaque shields that cover the stoppering station, metal or ceramic filling substrates, or combinations thereof. For example, the filling substrate may be a stainless steel manifold and/or black silicon sheet(s) may be used to cover all or a portion of the filling unit. It is preferable for the ambient light level during the filling of containers with the pharmaceutical composition to be less than about 10 lux, more preferably less than about 1 lux, even more preferably less than about 0.1 lux and most preferably less than 0.01 lux.

In a preferred embodiment, the pharmaceutical compositions is filled into containers having an opacity permitting about 10% or less of light from passing through the container, more preferably permitting about 5% or less of light or even more preferably about less than 1% of light from passing through the container, as measured using an opacimeter.

In a preferred embodiment, the pharmaceutical composition is exposed to about 6 hours or less of light during preparation of the composition and filling a container with the composition.

The selection of a container for storing the composition which is substantially opaque to light has been found to enable the prevention of the formation of oxidative degradants, in particular 6-(2-chlorophenyl)-6-oxohexanoic acid or a pharmaceutically acceptable salt thereof. Thus, in one embodiment, a method for preventing the formation of oxidative degradants, in particular 6-(2-chlorophenyl)-6-oxohexanoic acid or a pharmaceutically acceptable salt thereof, in a pharmaceutical composition comprising esketamine or a pharmaceutically acceptable salt thereof is provided comprising selecting a container for storing the pharmaceutical composition that has an opacity permitting about 10% or less of light from passing through the container, as measured using an opacimeter.

In a preferred embodiment, the method for preventing the formation of oxidative degradants in a pharmaceutical composition comprising esketamine or a pharmaceutically acceptable salt thereof comprises:

a) exposing the pharmaceutical composition to 6 hours or less of light during preparation of the composition;
b) selecting a container that has an opacity permitting about 10% or less of light from passing through the container, as measured using an opacimeter; and
c) filling said container with the pharmaceutical composition, preferably in the absence of light.

Preferably, said method further comprises storing the pharmaceutical composition in said container in the absence of light.

In further embodiments, the disclosure provides methods for reducing or preventing the formation of oxidative degradants when packaging the containers containing the pharmaceutical compositions. Desirably, the filled and stoppered containers are packaged in a second container that, itself, is opaque to light. The second container may be appropriately coated or lined with a foil or the like, and/or made from a material that is opaque to light. In some aspects, the second container is an aluminum bag.

In yet other embodiments, the disclosure provides methods for reducing or preventing the formation of oxidative degradants when storing the pharmaceutical compositions. As such, the containers alone or containers packaged within a second container are stored in the absence of light as described herein.

In still further embodiments, the disclosure provides methods for reducing or preventing the formation of oxidative degradants when handling the pharmaceutical compositions prior to administration.

Methods of Use

Unless otherwise noted, amounts of esketamine described herein are typically set forth on an esketamine free base basis. That is, the amounts indicate that amount of the esketamine molecule administered, exclusive of, for example, counterions (such as in pharmaceutically acceptable salts).

In certain embodiments, esketamine is administered intranasally. In further embodiments, esketamine is administered intranasally as its corresponding hydrochloride salt. In other embodiments, esketamine is administered intranasally as its corresponding hydrochloride salt in an 16.14% weight/volume solution (equivalent to 14% weight/volume of esketamine base).

In yet other embodiments, esketamine is administered intranasally as a solution comprising 161.4 mg/mL of esketamine hydrochloride (equivalent to 140 mg/mL of esketamine base), 0.12 mg/mL of ethylenediaminetetraacetic acid (EDTA), 1.5 mg/mL citric acid, at a pH of 4.5 in water, and (i) not more than about 0.2% (HPLC area) of an oxidative degradant or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof. In still further embodiments, esketamine is administered intranasally, wherein the intranasal delivery administers 100 μL of a solution comprising 161.4 mg/mL of esketamine hydrochloride (equivalent to 140 mg/mL of esketamine base), 0.12 mg/mL of EDTA, 1.5 mg/mL citric acid, at a pH of 4.5 in water, and (i) not more than about 0.2% (HPLC area) of an oxidative degradant or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof. In other embodiments, esketamine is delivered intranasally using a nasal spray pump, wherein the pump delivers 100 μL of a solution comprising 161.4 mg/mL of esketamine hydrochloride (equivalent to 140 mg/mL of esketamine base), 0.12 mg/mL of EDTA, 1.5 mg/mL citric acid, at a pH of 4.5 in water, and (i) not more than about 0.2% (HPLC area) of an oxidative degradant or a pharmaceutically acceptable salt thereof, relative to the amount of esketamine, (ii) not more than about 0.2% w/w of an oxidative degradant or a pharmaceutically acceptable salt thereof, relative to the weight of esketamine, or (iii) not more than about 120 ppm of an oxidative degradant or pharmaceutically acceptable salt thereof.

In general, a single pump from a nasal spray device may be configured to deliver about 50 μL to about 200 μL of an esketamine solution to a nostril of the subject, including about 60 μL, about 70 μL, about 80 μL, about 90 μL, about 100 μL, about 110 μL, about 120 μL, about 130 μL, about 140 μL, about 150 μL, about 160 μL, about 170 μL, about 180 μL, and about 200 μL. Accordingly, two pumps deliver about 100 μL to about 400 μL to the subject.

The present invention is further directed to utilizing the pharmaceutical o compositions described herein in methods for the treatment of depression, preferably resistant depression or treatment refractory depression, comprising administering to a subject in need thereof, a therapeutically effective amount of any of the pharmaceutical compositions a described herein. Preferably, the administration is nasal.

In an embodiment, the present invention is directed to a method for the treatment of depression, preferably resistant depression or treatment refractory depression, comprising the nasal administration of the pharmaceutical composition according to the invention as described herein to a subject in need thereof.

As used herein, the term "depression" shall be defined to include major depressive disorder, unipolar depression, treatment-refractory depression, resistant depression, anxious depression, bipolar depression and dysthymia (also referred to as dysthymic disorder). Preferably, the depression is major depressive disorder, unipolar depression, treatment-refractory depression, resistant depression, anxious depression or bipolar depression.

As used herein, the term "treatment-refractory or treatment-resistant depression" and the abbreviation "TRD" shall be defined as major depressive disorder that does not respond to adequate courses of at least two antidepressants, preferably two or more antidepressants, more preferably two to three, antidepressants.

As used herein, the term "bipolar depression" is intended to mean the depression associated with, characteristic of or symptomatic of a bipolar disorder. Thus, methods of treating bipolar depression of the present invention are directed to methods which treat the depression and/or depressed phase of bipolar disorders.

One skilled in the art will recognize that the failure to respond to an adequate course of a given antidepressant may be determined retrospectively or prospectively. In an embodiment, at least one of the failures to respond to an adequate course of antidepressant is determined prospectively. In another embodiment, at least two of the failures to respond to an adequate course of antidepressant are determined prospectively. In another embodiment, at least one of the failures to respond to an adequate course of antidepressant is determined retrospectively. In another embodiment, at least two of the failures to respond to an adequate course of antidepressant are determined retrospectively.

In an embodiment, the present invention is directed to methods for the treatment of depression in suicidal patients. One skilled in the art will recognize that the term "depression in suicidal patients" shall include any type of depression as herein defined, when diagnosed in a patient that also exhibits at least one symptom of suicidality, for example suicidal ideations and/or behaviors (e.g. intent, planning, etc.). Thus, "depression in suicidal patients" includes, but is not limited to, major depressive disorder in suicidal patients, unipolar depression in suicidal patients, treatment resistant depression in suicidal patients, depression with anxious distress in suicidal patients, bipolar depression in suicidal patients and dysthymia in suicidal patients. Preferably, the "depression in suicidal patients" is selected from the group consisting of major depressive disorder in suicidal patients, unipolar depression in suicidal patients and treatment resistant depression in suicidal patients. More preferably, the "depression in suicidal patients" is treatment resistant depression in suicidal patients.

As used herein, "suicide" is the "act of taking one's own life". See, http://en.wikipedia.org/wiki/Suicide-cite_note-7. Suicide includes attempted suicide or non-fatal suicidal behavior, which is self-injury with the desire to end one's life that does not result in death. Suicide attempt is a self-initiated sequence of behaviors by an individual who, at the time of initiation, expected that the set of actions would lead to his or her own death.

As used herein, "suicidal ideation" refers to thoughts about or an unusual preoccupation with suicide, or thoughts of ending one's life or not wanting to live anymore but not necessarily taking any active efforts to do so. The range of suicidal ideation varies greatly from fleeting to chronic and progresses to detailed planning, role playing, and unsuccessful attempts, which may be deliberately constructed to fail or be discovered, or may be fully intended to result in death.

As used herein, unless otherwise noted, the terms "treating", "treatment" and the like, shall include the management and care of a human patient for the purpose of combating a disease, condition, or disorder and includes the administration of a pharmaceutical composition of the present disclosure to prevent the onset of one or more symptoms or complications, alleviate one or more of the symptoms or complications, or eliminate the disease, condition, or disorder.

The term "therapeutically effective amount" as used herein, means that amount of active compound or pharmaceutical agent that elicits the biological or medicinal response in a human tissue system that is being sought by a researcher, medical doctor or other clinician, which includes alleviation of one or more of the symptoms of the disease or disorder being treated.

Optimal dosages to be administered may be readily determined by those skilled in the art, and will vary with the particular compound used, the mode of administration, the strength of the preparation, the mode of administration, the number of consecutive administrations within a limited period of time (e.g. up to 60 minutes) and the advancement of the disease condition. In addition, factors associated with the particular patient being treated, including patient age, weight, diet and time of administration, will result in the need to adjust dosages.

As used herein, the terms "co-therapy", "combination therapy", "adjunctive treatment", "adjunctive therapy", "combined treatment", and "co-administration" shall mean treatment of a patient in need thereof by administering esketamine in combination with one or more antidepressant(s), wherein esketamine and the antidepressant(s) are administered by any suitable means. In some embodiments, the esketamine pharmaceutical composition is administered in a regimen with one to five antidepressants. In other embodiments, the esketamine pharmaceutical composition is administered in a regimen with one, two, three, four, or five antidepressants. In other embodiments, the esketamine pharmaceutical composition is administered in a regimen with one or two antidepressants. In further embodiments, the esketamine pharmaceutical composition is administered in a regimen with the antidepressant currently being administered to the patient. In other embodiments, the esketamine pharmaceutical composition is administered in a regimen with a different antidepressant. In yet further embodiments, the esketamine pharmaceutical composition is administered in a regimen with an antidepressant not previously administered to the patient. In still other embodiments, the esketamine pharmaceutical composition is administered in a regimen with an antidepressant previously administered to the patient. Where the esketamine pharmaceutical composition and the antidepressant(s) are administered in separate dosage forms, the number of dosages administered per day for each compound may be the same or different and more typically different. The antidepressant may be dosed as prescribed by the attending physician and/or by its label and the esketamine pharmaceutical composition is dosed as described herein. Typically, a patient is under concurrent treatment with both an antidepressant and esketamine, where both are administered by their prescribed dosing regimens.

The esketamine pharmaceutical composition and the antidepressant(s) may be administered via the same or different routes of administration. Examples of suitable methods of administration include, but are not limited to, oral, intravenous (iv), intranasal (in) intramuscular (im), subcutaneous (sc), transdermal, buccal, or rectal. In some embodiments, esketamine is administered intranasally. As used herein, unless otherwise noted, the term "antidepressant" shall mean any pharmaceutical agent which can be used to treat depression. Suitable examples include, without limitation, a mono-amine oxidase inhibitor, tricyclic, serotonin reuptake inhibitor, serotonin noradrenergic reuptake inhibitor, noradrenergic and specific serotonergic agent, or atypical antipsychotic. Other examples include, but are not limited to mono-amine oxidase inhibitors such as phenelzine, tranylcypromine, moclobemide, and the like; tricyclics such as imipramine, amitriptyline, desipramine, nortriptyline, doxepin, protriptyline, trimipramine, clomipramine, amoxapine, and the like; tetracyclics such as maprotiline, and the like; non-cyclics such as nomifensine, and the like; triazolopyridines such as trazodone, and the like; serotonin reuptake inhibitors such as fluoxetine, sertraline, paroxetine, citalopram, citalopram, escitalopram, fluvoxamine, and the like; serotonin receptor antagonists such as nefazadone, and the like; serotonin noradrenergic reuptake inhibitors such as venlafaxine, milnacipran, desvenlafaxine, duloxetine, levomilnacipran and the like; noradrenergic and specific serotonergic agents such as mirtazapine, and the like; noradrenaline reuptake inhibitors such as reboxetine, edivoxetine and the like; atypical antipsychotics such as bupropion, and the like; natural products such as Kava-Kava, St. John's Wort, and the like; dietary supplements such as s-adenosylmethionine, and the like; and neuropeptides such as thyrotropin-releasing hormone and the like; compounds targeting neuropeptide receptors such as neurokinin receptor antagonists and the like; and hormones such as triiodothyronine, and the like. In some embodiments, the antidepressant is imipramine, amitriptyline, desipramine, nortriptyline, doxepin, protriptyline, trimipramine, maprotiline, amoxapine, trazodone, bupropion, clomipramine, fluoxetine, duloxetine, escitalopram, citalopram, sertraline, paroxetine, fluvoxamine, nefazadone, venlafaxine, milnacipran, reboxetine, mirtazapine, phenelzine, tranylcypromine, moclobemide, Kava-Kava, St. John's Wart, s-adenosylmethionine, thyrotropin releasing hormone, a neurokinin receptor antagonist, or triiodothyronine. Preferably, the antidepressant is selected from the group consisting of fluoxetine, imipramine, bupropion, venlafaxine and sertraline.

Therapeutically effective amounts/dosage levels and dosage regimens for antidepressants (for example, mono-amine oxidase inhibitors, tricyclics, serotonin reuptake inhibitors, serotonin noradrenergic reuptake inhibitors, noradrenergic and specific serotonergic agents, noradrenaline reuptake inhibitor, natural products, dietary supplements, neuropeptides, compounds targeting neuropeptide receptors, hormones and other pharmaceutical agents disclosed herein), may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http:///www.pdrel.com) or other sources.

The therapeutically effective amount of esketamine and/or antidepressant may be administered during an initial phase(s) and/or subsequent phase(s) as described U.S. Patent Application Publication No. 2016/0338977 and International Patent Publication No. WO-2019/126108, incorporated herein by reference. In some embodiments, the therapeutically effective amount of esketamine is about 20 to about 100 mg. In other embodiments, the therapeutically effective amount of esketamine is about 30 to about 90 mg. In further embodiments, the therapeutically effective amount of esketamine is about 40 to about 80 mg. In yet other embodiments, the therapeutically effective amount of esketamine is about 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg. In further embodiments, the therapeutically effective amount is about 28 mg, about 56 mg, or about 84 mg. In other embodiments, the therapeutically effective amount is about 56 mg or about 84 mg. In yet further embodiments, the therapeutically effective amount of esketamine is about 28 mg. In other embodiments, the therapeutically effective amount of esketamine is about 56 mg. In still further embodiments, the therapeutically effective amount is of esketamine about 84 mg.

Abbreviations

SEM: Scanning electron microscopy
EDX: Energy-Dispersive X-ray
IR-ATR: Infrared-Attenuated Total Reflectance
LC-MS: Liquid chromatography mass spectrometry
THF: tetrahydrofuran
UV-Vis: Ultraviolet-visible
SPE: Solid Phase Extraction
MS: Mass Spectrometry
RT: Retention Time
STD: Standard
CCT: Collision Cell Technology
ATR: Attenuated Total Reflectance
IR: infrared
LC-DAD-MS: Liquid Chromatography-Diode-Array Detector-mass spectrometry
ICH: International Conference for Harmonization
D50: standard illuminant with a color temperature of 5000 K; approximate intensity ~210 fc
AU: absorbance unit
ICP-MS: Inductively coupled plasma mass spectrometry
lux hour: unit of illuminance per hour

EXAMPLES

Esketamine nasal spray formulations consisted of 161.4 mg/mL esketamine hydrochloride (equivalent to 140 mg of esketamine base) formulated in 0.12 mg/mL ethylenediaminetetraacetic acid (EDTA) and 1.5 mg/mL citric acid at a pH of 4.5 in water.

The following samples were utilized in the Examples set forth below.

Sample 1: vials of esketamine nasal spray, drug product batch 1, showing yellow/brown discoloration.

(i) one bag with vials labelled "less discolored"

(ii) one bag with vials labelled "severe discoloration"

Sample 2: Vials of esketamine nasal spray, drug product batch 1, without discoloration—vials were removed from nasal spray devices.

Sample 3: Vials of esketamine nasal spray, drug product batch 2, without discoloration.

Sample 4: Vials of esketamine nasal spray, drug product batch 3, without discoloration.

Sample 5: Vials of esketamine nasal spray, drug product batch 4 without discoloration.

Sample 6: Two different grip seal bags used to store (retain) samples (i) Grip seal bags with a blue zone at the grip seal location.

(ii) Grip seal bags without a blue zone at the grip seal location.

For the qualitative investigation, only vials of esketamine with discoloration (e.g. Sample 1, both bags) and without discoloration (reference, e.g. Sample 2) from the same lot (batch 1) were used.

Example 1: Glass Delamination

The possibility of glass delamination of the glass vials containing discolored sample was tested and compared with reference vials not containing discolored sample. For this purpose, the esketamine solution and plunger stopper were extracted from a vial of batch 1 showing discoloration (i.e. Sample 1) and from a vial of the same batch not showing any discoloration (i.e. Sample 2). Both vials were rinsed with 0.1 M HCl, ethanol and pure water. The vials were filled with 1.25 mg/mL methylene blue solution, which is known to adsorb to delaminated glass. After shaking and an incubation of 5 minutes, the vials were emptied and rinsed with pure water to remove all methylene blue. Visual checks of the vials were performed to verify whether methylene blue adsorbed onto the glass and thus glass delamination had occurred.

Visual checks of the vials that were treated with methylene blue showed no differences between the discolored and the not discolored samples. Both vials showed very small rings at the height of the stopper but not at the height of the solution.

The glass delamination test showed no visual differences between the discolored and the not discolored samples of esketamine. The level of glass delamination is therefore considered to be the same.

Example 2: Stopper Integrity Testing

Stoppers from 4 discolored vials (i.e. Sample 1) were removed using a needle tool, but care was taken not to damage the thin central part of the stopper. The stoppers were microscopically examined to check the integrity of the stopper.

None of the investigated stoppers of the discolored vials (i.e. Sample 1) showed evidence that the stoppers were pierced or damaged in some other way.

Based on stereomicroscope images of the vials of esketamine batch 1 (both less and severe discolored) many floating brown particles could be observed and also some deposit on the inside vial wall, partially formed of small bubbles. Also rubber stoppers were observed to have some yellow/brown discoloration on the surface in contact with liquid.

Based on microscopic analysis the particles are irregular and appear as thin films with different levels of yellow/brown color.

Based on IR microscopy analysis the particles could be identified as silicone-based. Additional features in the spectra of the particles could not be identified although some slight resemblance to the esketamine spectrum could be seen in certain spectral regions.

The yellow/brown material was observed not to dissolve in dichloromethane but in THF. After washing with dichloromethane, the outline of the particle was still visible, but has slightly faded. The color did not change. Based on IR analysis of the remaining yellow/brown material, the silicone bands are no longer present, but it could not be identified. It is believed that the brown material consists of very small particles.

Based on microscope and IR analysis it was shown that the silicone particles adsorb onto the stopper surface for vials showing discoloration most likely due to the high affinity of silicone particles for the siliconized rubber stopper surface and that they could be partially removed by washing with ethanol.

Example 3: Transmission Profile of Plastic Grip Seal Bags

UV-Vis spectra were recorded from 3 pieces from each bag from Sample 6 using a Unicam UV 500 (Thermo Spectronic) UV-Vis spectrometer.

Two types of grip seal bags are used to store samples. Only slight differences could be noted in the transmission profiles of the two bags.

Example 4: Analysis of the Discoloration

Optical pictures were taken with a Leica MZ16 stereomicroscope and/or a Leica DMLM microscope. Scanning electron microscope (SEM) imaging and energy-dispersive X-ray (EDX) analysis was performed with a Hitachi TM3000 scanning electron microscope equipped with a Bruker Quantax 70 EDX detector in charge reduction mode at 5 kV and 15 kV (EDX reporting threshold of 0.2% was applied). Samples were sputter coated with Au/Pd using a Quorum SC7620 sputter coater.

Infrared (IR) analysis was performed with a Bruker Hyperion 3000 Infrared Microscope connected to a Tensor 27 spectrometer. A 20× ATR objective was used to record the IR spectra.

A. Analysis of Vial Content

The contents of selected vials were filtered using a vacuum filtration unit through a 0.1 m Whatman Anodisc filter followed by washing with 0.1 M HCl and water. By using a needle tool some material was collected from the inside of the emptied, rinsed and dried esketamine discolored vial. A small amount of the material was transferred onto a gold-plated mirror for IR analysis.

In the discolored vials of Sample 1, many floating brown particles could be observed and also some deposit on the inside vial wall, partially formed of small bubbles. Also rubber stoppers were observed to have some yellow/brown discoloration on the side in contact with liquid (less for stoppers from vials classified as "less discolored"). No discoloration can be observed on the reference stopper nor any floating particles.

Microscope images of selected isolated particles on the filter (from Sample 1) show that some particles are smoother and seem less brown colored.

The particles isolated on the filter appear as curled thin films of brown material. Some particles are smoother and seem to be less brown colored.

SEM (backscatter electron) images of selected particles were obtained. All particles have an irregular shape. Particles are flat with some irregularities on the edges. When imaged at 15 kV they show less contrast. The particles appear "semitransparent" meaning that despite Au/Pd coating, the electron beam is partially going through them, indicating that they are very thin.

IR-ATR spectra of the isolated particles both on the Whatman Anodisc filter after filtration of the discolored vial content, and scraped off from the inside of a vial showing discoloration were recorded for identification purposes. The brown particles could be identified as silicone-based.

B. Stoppers Analysis

Stoppers were microscopically examined. Two reference (from Sample 2) and two severe discolored vials (from Sample 1) were selected from the sample bags. Stoppers were removed from the vials using a needle tool. Each stopper was washed with 0.1 M HCl and particle-free water. Additionally one reference and one severe discolored stopper were washed in ethanol. From each stopper a piece that was in contact with liquid in the vial, was cut out using a scalpel tool and attached to an adhesive carbon pad attached to an aluminum SEM stub. After IR analysis, the SEM sample holder with 4 stoppers was coated using a sputter coater with Au/Pd and imaged with SEM.

Images of a discolored stopper (isolated from a vial of Sample 1) and its cross-section were obtained. Specifically, images were obtained of (A) the discolored side that was in contact with the esketamine solution) of the stopper from a vial of esketamine nasal spray of batch 1, (B) the other side of the stopper (regular color) that was not in contact with the esketamine solution; (C) an isolated discolored stopper; (D) a cross-section of the stopper—no migration of the color into the stopper could be seen.

Discoloration of the stopper is observed up to the first rim, this is the area that is in contact with the drug product in the vial. No clear discoloration can be observed on the cross-section indicating that the discoloration is most likely only a surface effect (adsorption of brown substance onto stopper surface).

Images of HCl and water washed reference and discolored stoppers from esketamine nasal spray of batch 1 were obtained. Images of the reference and discolored stopper additionally washed in ethanol were also obtained. A clear difference between discolored stoppers as compared to reference stoppers could be seen. However it is clearly visible that ethanol washing is removing part of the material on the stopper.

IR-ATR spectra of each stopper, collected from three different points, were recorded for identification purposes. Based on IR microscope analysis in all spectra apart from the rubber stopper material, an additional contribution of silicone could be seen. The presence of silicones can be linked to the stopper silicone coating. In the spectra of the reference stoppers (washed with HCl and water or HCl, water and ethanol), and the discolored stopper (washed with HCl, water and ethanol) the silicone contribution was minor. The IR spectra from the discolored stopper (washed only with HCl and water) corresponds mainly to silicones, the contribution of stopper rubber material is limited. However, when the stopper was washed additionally with ethanol, silicone contribution decreases and rubber becomes more apparent. This indicates that silicone particles adsorb onto the stopper surface for vials showing discoloration. Based on SEM analysis of the sputter coated stoppers, there were no differences observed between discolored and reference stoppers treated in the same way.

C. Solubility Testing

A small amount of $CH_2Cl_2$ was added to one discolored vial (Sample 1) while tetrahydrofuran (THF) was added to another vial of the same sample. Both vials were re-stoppered, shaken and observed visually. In an additional experiment, some of the particles isolated (from Sample 1) on the Whatman Anodisc filters were washed with dichloromethane ($CH_2Cl_2$) and THF to evaluate the solubility.

Upon addition of $CH_2Cl_2$ to the discolored solution (Sample 1) it could be noticed that the yellow/brown color transferred to the $CH_2Cl_2$ phase. Upon visual and microscopic (stereomicroscope) investigation, no particles were observed in the $CH_2Cl_2$ solution. When the same test was repeated with THF, the solution stayed yellow/brown and also here, upon visual and microscopic (stereomicroscope) investigation, no particles were observed in the solution.

Images of an isolated particle (isolated from a vial of Sample 1 on a Whatman Anodisc filter) before and after $CH_2Cl_2$ washing were obtained. A slight difference in appearance of the particle is noted upon washing with $CH_2Cl_2$ (the outline of the particle is still visible, but has slightly faded). No removal of the brown color is noted. However, when a filter with isolated particles (from a vial of Sample 1) was rinsed with THF, the brown color disappeared almost completely.

IR-ATR spectra of the $CH_2Cl_2$ washed particles were recorded for identification purposes. The silicone bands are no longer present, and only the additional bands (which were initially also present) remain. The silicone part of the particle is removed leaving behind only the brown material.

With this experiment it was shown that the silicone part of the particles dissolves in $CH_2Cl_2$. The brown substance does not dissolve in $CH_2Cl_2$, but dissolves in THF. No particles were observed after addition of $CH_2Cl_2$ to a discolored vial, and washing does not remove the brown color from the filter.

D. Stressed Samples (ICH Light)

One vial of not discolored esketamine batch 1 was exposed to two cycles of ICH light for 8 hours at 700 W/$m^2$ (total 16 hours) followed by keeping it at 70° C. in an oven for 3 months (in dark). A $2^{nd}$ vial was kept as a reference at the same oven condition without exposure to light. Pictures of the vials were taken with a Leica MZ16 stereomicroscope. The samples were further subjected to LC-DAD-MS analysis in order to evaluate the degradation product pattern.

Images of both stressed and not stressed vials of esketamine batch 1 were obtained for (A) stressed vial of Esketamine batch 1—exposed to ICH light and (B) a vial that was not exposed to light. Both vials were kept at the same oven conditions (3 months at 70° C.).

The solution in the esketamine vial that was exposed to light (and stored for 3 months at 70° C.) is discolored to a yellow/brown color and floating particles can be seen. The appearance is visually similar to what was observed earlier in the discolored vials of batch 1.

In the solution of the esketamine vial that was not exposed to light (but kept at the same oven conditions for the same time period), no discoloration was observed and no floating particles could be seen.

As a comparison, images of one less discolored and one severely discolored esketamine vial of batch 1 (i.e. Sample 1) were obtained. The content of all 4 vials was further analyzed with LC-DAD-MS. Based on the LC-DAD-MS analysis on the light/thermal stress vial and thermal stress vial of batch 1 and the appearance of fine particles in the light/thermal stress vial, one can conclude that light irradiation is a potential root cause for the observed yellow/brown discoloration.

E. Liquid Chromatography—Diode Array Detection—Mass Spectrometry (LC-DAD-MS)

Liquid chromatography mass spectrometry (LC-MS) analyses were performed on retained samples and stressed samples after dilution, as well as on solid phase extracts. In case of dilution, the samples were diluted with acetonitrile by a factor of 50 before analysis.

For the solid phase extraction experiment, samples were prepared as follows: the content of three selected vials showing yellow/brown discoloration (Sample 1) was subjected to solid-phase extraction using a SEP-PAK C18 cartridge (Waters). A step gradient of increasing solvent strength was used to elute analytes based on differences in polarity. The same procedure was executed for three vials of the reference sample (Sample 2).

An emptied vial of sample 1 was rinsed with 0.1 M HCl and water. The colored residue on the inner surface of the vial was dissolved in a small amount of tetrahydrofuran (THF).

LC-MS analyses were performed using a Dionex Ultimate 3000 HPLC system equipped with a diode array detector, coupled to a Thermo Q Exactive Plus orbitrap mass spectrometer.

Chromatographic separations were performed on a 150 mm×3.0 mm ID Waters XBridge C18 3.5 μm column. The column heater was kept at 45° C. and the flow rate was 0.6 mL/min. Eluent A consisted of 10 mM ammonium acetate and eluent B was acetonitrile. The gradient elution comprised a linear gradient of 10 to 100% eluent B over 12 minutes, and was kept for 5 minutes at 100% B.

High resolution accurate mass data were acquired in both positive and negative ion mode using an electrospray ionization source. Identifications were accomplished by manual interpretation of the spectra and via comparison with spectra of reference materials.

After solid phase extraction the yellow/brown colored species were mainly concentrated in one fraction. LC-DAD-MS analysis of this concentrated fraction, as well as analysis of the residue dissolved in THE demonstrates the presence of several compounds with a UV-Vis spectrum that shows absorption bands between 380 and 430 nm. Absorption in this wavelength region renders a substance yellow/brown, so in the chromatograms with a wavelength selection from 380 to 430 nm the yellow colored analytes are selectively visible.

The chromatogram of the concentrated SPE fraction shows several peaks between 3.5 and 6.5 minutes. None of these peaks were present in the SPE fraction of the non-colored reference sample. The chromatogram of the residue shows two peaks at RT 9.35 and 11.19 minutes.

The mass spectra of the colored analytes except one show a chlorine isotope pattern. Moreover an examination of the fragmentation patterns of obtained MS/MS spectra allows impurities structural information to be associated with that of the active pharmaceutical ingredient esketamine.

A total impurity profile evaluation of the discolored sample shows predominantly the presence of a peak at retention time (RT) 4.97 minutes, while this peak is not present in the chromatogram of the non-colored reference sample (see FIG. 1). Furthermore, the total wavelength chromatogram shows that the yellow colored analytes represent only a small fraction of the analytes present in the concentrated fraction as also other non-colored analytes have been concentrated.

The impurity at RT 4.97 minutes had an observed accurate mass of m/z 239.04750 Da $[M-H]^-$ which corresponds to the formula $C_{12}H_{12}O_3Cl$. A product ion scan of a 239.05 molecular weight was performed to provide structural information for this impurity. The obtained mass spectral data suggested the analyte to be 6-(2-Chlorophenyl)-6-oxo-hexanoic acid. The identity was confirmed based upon both retention time and mass spectrometric data match by analysis of commercially available 6-(2-Chlorophenyl)-6-oxo-hexanoic acid purchased from Rieke Metals.

The formation of 6-(2-chlorophenyl)-6-oxohexanoic acid was previously reported during forced degradation testing in the presence of hydrogen peroxide and in the presence of a radical initiator.

LC/MS analysis of the yellow/brown light/thermal stress sample (ICH light) and the colorless thermal stress sample was performed. The light stressed sample shows a mainly similar degradation profile in comparison with that of a vial from batch 1 showing discoloration. The major degradant in the light stressed sample was shown to be 6-(2-chlorophenyl)-6-oxohexanoic acid. Some other oxidative degradants and noresketamine were present as well. 6-(2-chlorophenyl)-6-oxohexanoic acid was also found in the non-light stressed sample but in much lower quantities. An overlay of the different samples is shown in FIG. 1.

Besides the yellow/brown colored species, the major impurity is identified as being 6-(2-Chlorophenyl)-6-oxo-hexanoic acid.

Example 4: Quantitative Investigations

ICP-MS quantitative analyses were carried out on a Thermo XSeries 2 quadrupole ICP-MS. The instrument was operated in standard (STD) and Collision Cell Technology (CCT) mode. Rh (measured in STD mode) or Rh (measured in STD mode) in combination with Y (measured in CCT mode) was used as an internal standard. ICP Multi-Element Standard Merck IV (containing Li, B, Na, Mg, Al, K, Ca, Cr, Mn, Fe, Co, Ni, Cu, Zn, Ga, Sr, Ag, Cd, In, Ba, Ti, Pb, Bi) or Multi-Element Standard Merck IV in combination with Sn Standard were used for calibration. The calibrated elements were measured in a fully quantitative analysis; the remaining elements were measured in a semi quantitative analysis.

A. Metal Concentrations Present in Drug Product Solutions

To assess to what extent the observed yellow/brown discoloration is due to the presence of elemental impurities, the content of vials taken from the batch showing discoloration (batch 1 i.e. Sample 1) and the content of vials from batches not showing any discoloration (batch 1/Sample 2, batch 2/Sample 3, batch 3/Sample 4, batch 4/Sample 5) was analyzed using ICP-MS. The content of each vial was collected by means of a stainless steel needle mounted on a plastic syringe (both pre-rinsed with ultrapure water). A sample volume of ca. 0.2 mL was mixed with 0.1 mL of concentrated $HNO_3$ (69%) and ultrasonicated at 50° C. for 5 minutes. After having undergone this treatment, the sample was adjusted to 5 mL with ultrapure water and subjected to ICP-MS analysis.

A full elemental analysis was performed by ICP-MS. No observable differences in metal concentrations could be seen between vial contents that showed (medium or high)discoloration (samples from batch 1) and vial contents that did not show discoloration (samples from batches 1-4). The metals present in the esketamine samples for which the average measured concentration in at least one batch was above 0.01 μg/mL are summarized in Table 1A-1B. Average Na concentrations in vials of the different batches were above 200 μg/mL, while average measured B concentrations were between 1.5 and 2.5 μg/mL. The average levels of Mg were somewhat higher in vials showing discoloration (1.1-1.5 μg/mL) compared with vials not showing any discoloration (0.58-0.82 μg/mL). However, when comparing individual Mg values of samples not showing discoloration with samples showing discoloration, these differences were not pronounced. Average concentrations of Al were between 0.62 and 0.75 μg/mL, while average concentrations of Fe were between 0.13 and 0.32 μg/mL. The average levels of Cr, Ni, Zn, Ga, As, Zr, Ba were below 0.06 μg/mL for the different batches. For Si, no exact concentrations are indicated since Si was only determined in a semi-quantitative analysis and has known interferences. However, the levels of Si were very comparable in the not discolored and discolored samples.

TABLE 1A

Average metal concentrations with standard deviations for the number of individually sampled solutions from vials (N) are indicated for solutions showing no discoloration (from batches 1-4) and solutions showing medium (from batch 1) and high discoloration (from batch 1).

| | | Element | | | | | |
|---|---|---|---|---|---|---|---|
| | | B | Na | Mg | Al | Cr | Fe |
| | | Batch 2 | | | | | |
| No Discoloration | Average (μg/mL) | 2.40 | 281 | 0.62 | 0.63 | 0.02 | 0.31 |
| | stdev (μg/mL) | 1.20 | 106 | 0.27 | 0.27 | 0.01 | 0.13 |
| | N | 8 | 8 | 8 | 8 | 8 | 8 |
| | | Batch 3 | | | | | |
| | Average (μg/mL) | 1.97 | 307 | 0.82 | 0.71 | 0.01 | 0.15 |
| | stdev (μg/mL) | 0.32 | 39 | 0.16 | 0.21 | 0.01 | 0.03 |
| | N | 8 | 8 | 8 | 8 | 8 | 8 |

TABLE 1A-continued

Average metal concentrations with standard deviations for the number of individually sampled solutions from vials (N) are indicated for solutions showing no discoloration (from batches 1-4) and solutions showing medium (from batch 1) and high discoloration (from batch 1).

| | | Element | | | | | |
|---|---|---|---|---|---|---|---|
| | | B | Na | Mg | Al | Cr | Fe |
| | Batch 4 | | | | | | |
| | Average (μg/mL) | 2.11 | 275 | 0.58 | 0.62 | 0.01 | 0.27 |
| | stdev (μg/mL) | 0.20 | 22 | 0.13 | 0.20 | 0.01 | 0.04 |
| | N | 8 | 8 | 8 | 8 | 8 | 8 |
| | Batch 1 | | | | | | |
| | Average (μg/mL) | 1.86 | 321 | 0.66 | 0.75 | 0.01 | 0.14 |
| | stdev (μg/mL) | 0.20 | 32 | 0.18 | 0.10 | 0.01 | 0.07 |
| | N | 11 | 11 | 11 | 11 | 11 | 11 |
| Discoloration | Batch 1 | | | | | | |
| | Average (μg/mL) | 1.70 | 289 | 1.13 | 0.68 | 0.01 | 0.17 |
| | stdev (μg/mL) | 0.21 | 9 | 0.23 | 0.11 | 0.01 | 0.06 |
| | N | 3 | 3 | 3 | 3 | 3 | 3 |
| | Batch 1 | | | | | | |
| | Average (μg/mL) | 1.59 | 284 | 1.49 | 0.64 | 0.01 | 0.13 |
| | stdev (μg/mL) | 0.11 | 11 | 0.18 | 0.05 | 0.01 | 0.01 |
| | N | 3 | 3 | 3 | 3 | 3 | 3 |

In these experiments each solution was sampled from the vial using a needle and syringe and analyzed individually.

TABLE 1B

Average metal concentrations with standard deviations for the number of individually sampled solutions from vials (N) are indicated for solutions showing no discoloration (from batches 1-4) and solutions showing medium (from batch 1) and high discoloration (from batch 1).

| | | Element | | | | | |
|---|---|---|---|---|---|---|---|
| | | Ni | Zn | Ga | As | Zr | Ba |
| | Batch 2 | | | | | | |
| No Discoloration | Average (μg/mL) | 0.01 | 0.01 | <0.01 | 0.05 | <0.01 | 0.01 |
| | stdev (μg/mL) | 0.01 | 0.01 | | 0.02 | | 0.01 |
| | N | 8 | 8 | 11 | 8 | 11 | 8 |
| | Batch 3 | | | | | | |
| | Average (μg/mL) | 0.01 | 0.03 | <0.01 | 0.05 | <0.01 | 0.03 |
| | stdev (μg/mL) | 0.01 | 0.01 | | 0.01 | | 0.01 |
| | N | 8 | 8 | 8 | 8 | 8 | 8 |
| | Batch 4 | | | | | | |
| | Average (μg/mL) | 0.01 | 0.04 | 0.01 | 0.05 | <0.01 | 0.04 |
| | stdev (μg/mL) | 0.01 | 0.02 | 0.01 | 0.01 | | 0.01 |
| | N | 8 | 8 | 8 | 8 | 8 | 8 |
| | Batch 1 | | | | | | |
| | Average (μg/mL) | 0.01 | 0.01 | 0.02 | 0.04 | 0.01 | 0.01 |
| | stdev (μg/mL) | 0.01 | 0.01 | 0.01 | 0.01 | 0.01 | 0.01 |
| | N | 11 | 11 | 8 | 11 | 8 | 11 |
| Discoloration | Batch 1 | | | | | | |
| | Average (μg/mL) | 0.02 | 0.02 | <0.01 | 0.04 | <0.01 | 0.01 |
| | stdev (μg/mL) | 0.01 | 0.01 | | 0.01 | | 0.01 |
| | N | 3 | 3 | 3 | 3 | 3 | 3 |
| | Batch 1 | | | | | | |
| | Average (μg/mL) | 0.01 | 0.01 | <0.01 | 0.03 | <0.01 | 0.01 |
| | stdev (μg/mL) | 0.01 | 0.01 | | 0.01 | | 0.01 |
| | N | 3 | 3 | 3 | 3 | 3 | 3 |

In these experiments each solution was sampled from the vial using a needle and syringe and analyzed individually.
Blank fields in stdev rows mean that it was not determined as measured value was below detection limit.

ICP-MS analysis of esketamine solutions showed no observable differences in metal concentrations between vial contents showing discoloration (samples from batch 1) and vial contents not showing discoloration (samples from batches 1-4).

B. Metal Concentrations Present in Drug Products of Batches 5-7

To assess whether there is a link between metal concentrations and discoloration under light stress, the metal concentrations of samples from the same batches as those used in the light stress study (batches 5-7) were analyzed using ICP-MS. The collection of the sample content from the vial, sample treatment and sample dilution were performed in the same way as described in the previous paragraph.

A full elemental analysis was performed by ICP-MS. The main elements of interest are indicated in Table 2. In this table the measured concentrations in batches 5-7 are shown. For the screening results, average values and standard deviations were calculated based on 3 replicate sample preparations (1 Esketamine vial/sample preparation) and measurements. The average Fe concentration in batch 7 was higher than 1 μg/mL, while it was lower than 1 μg/mL in batches 5 and 6. The average Cr concentration was between 0.4 and 0.9 μg/ml in batches 6 and 7, while it was below 0.1 μg/mL in batch 5. The average Ni and Cu concentrations were below 0.1 μg/mL in the different batches. The average measured concentrations of B, Na, Mg, Si, Ca in the different batches were above 1 μg/mL.

TABLE 2

Average metal concentrations with standard deviations for three replicate solutions are indicated for the different batches which were also used in the light stress study.

| | Element | | | |
|---|---|---|---|---|
| | Cr | Fe | Ni | Cu |
| **Batch 6** | | | | |
| Average (μg/mL) | 0.45 | 0.77 | 0.06 | 0.01 |
| stdev (μg/mL) | 0.01 | 0.27 | 0.01 | 0.01 |
| N | 3 | 3 | 3 | 3 |
| **Batch 5** | | | | |
| Average (μg/mL) | 0.05 | 0.64 | 0.04 | 0.01 |
| stdev (μg/mL) | 0.02 | 0.22 | 0.02 | 0.01 |
| N | 3 | 3 | 3 | 3 |
| **Batch 7** | | | | |
| Average (μg/mL) | 0.87 | 1.30 | 0.07 | 0.01 |
| stdev (μg/mL) | 0.03 | 0.04 | 0.1 | 0.01 |
| N | 3 | 3 | 3 | 3 |

In these experiments each solution was sampled from the vial using a needle and syringe and analyzed individually.

C. Light Stress Study

In order to compare the influence of light for different esketamine drug product batches, a light stress study was initiated.

The following batches were included in the study:

(i) drug product batch 1 from Sample 2, (ii) drug product batch 5 (containing esketamine hydrochloride), (iii) drug product batch 6 (containing esketamine hydrochloride), this was also used to prepare a drug product solution for the study without stopper, (iv) drug product batch bulk 7 (containing esketamine hydrochloride), vials from this batch were on stability before this study and were stored and different temperatures and humidity.

From each batch, 3 vials were used:

(i) For the light cabinet one is placed upwards (stopper at the top), one downwards (stopper at the bottom), and one flat.

(ii) For the ICH light exposure and storage at 70° C., they were placed next to each other flat (iii) For the study without stopper they were all placed upwards (closed with paraffin on top)

Samples were placed at different conditions as shown in Table 3.

TABLE 3

Overview of different conditions for the light stress study for different esketamine batches

| | Batch | | | | |
|---|---|---|---|---|---|
| Conditions | 5 | 6 | 7 | 1 | No stopper |
| Dark + RT | Y | Y | Y | Y | Y |
| 2 × ICH + Dark RT | Y | Y | Y | Y | |
| 15 days D50 light + dark + RT | | Y | Y | | |
| D50 continuous | Y | Y | Y | Y | Y |
| 2 × ICH + dark + 70° C. | Y | | | Y | |
| dark + 70° C. | | | | Y | |

Notes:
dark = no light exposure;
ICH = ICH light for 8 hours at 700 W/m$^2$ (total 16 hours);
$D_{50}$ = exposure in a light cabinet with $D_{50}$ light At regular time intervals, the vials were visually examined and the color was compared against a color scale (Janssen Pharmaceutica, Appearance Guide for Solids, yellowish-brown grades, scale from 1 to 9, 2015) and a placebo vial (not colored).

For data evaluation, results from vials of the same batch which were exposed to the same light exposure condition/time were averaged together.

After finishing the light exposure, the contents of vials from all 4 batches that were oriented flat and continuously exposed to D50 light, were filtered using a vacuum filtration unit through a 0.1 μm Whatman Anodisc filter followed by washing with water.

Optical pictures were taken with a Leica MZ16 stereomicroscope and Leica DMLM microscope. Infrared (IR) analysis was performed with a Bruker Hyperion 3000 Infrared Microscope connected to a Tensor 27 spectrometer. A 20x ATR objective was used to record the IR spectra. At the end of the study, LC-DAD-MS was performed on a selected number of vials.

(i) Continuous Light Stress

Figure 2:
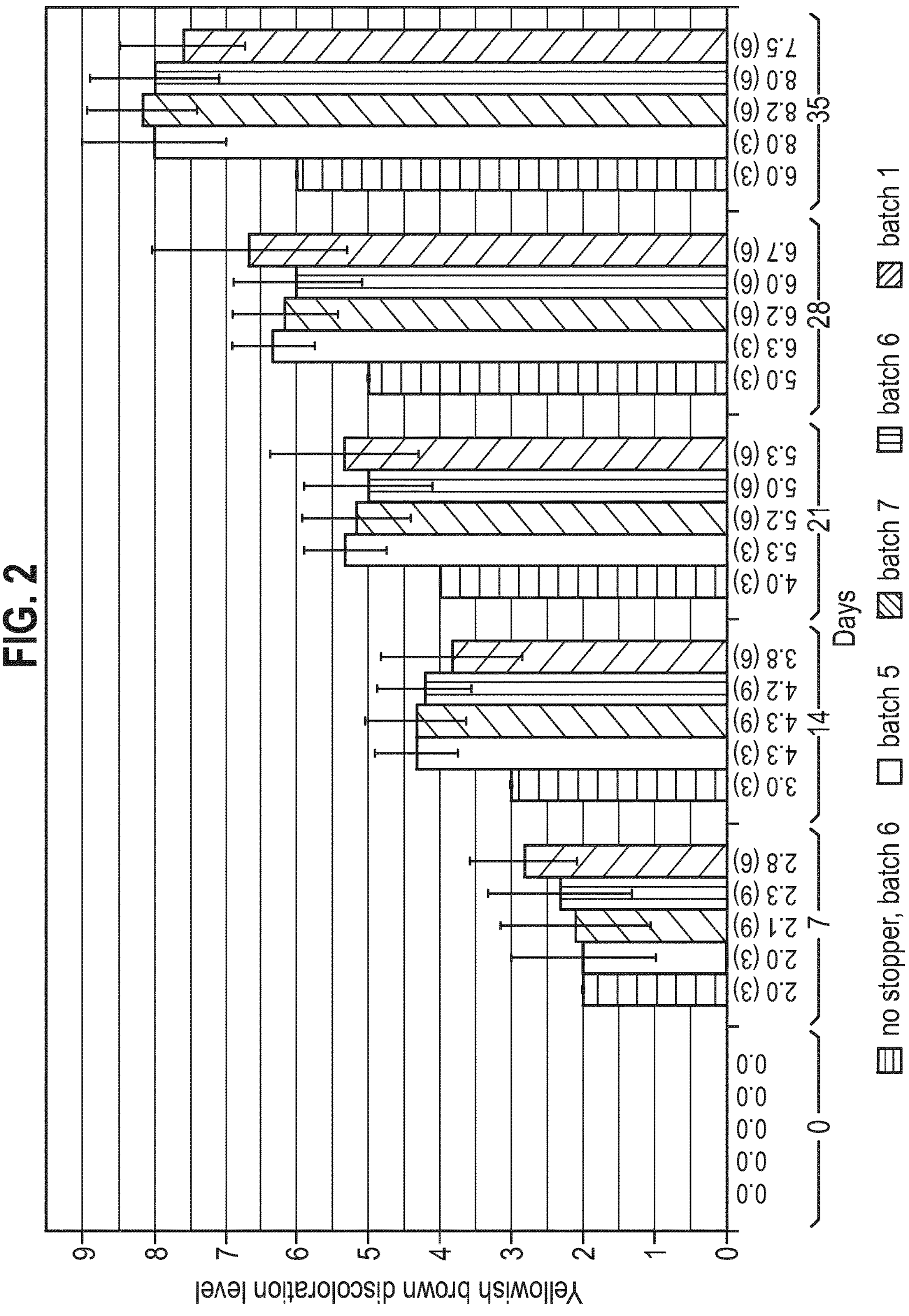
FIG. 2 is a bar graph comparing observed color changes of the vials from different esketamine batches exposed continuously to D50 light (in the vials without stopper and of batch 6, the same esketamine hydrochloride batch was used). The values in brackets indicate how many vials were used to calculate the average.

The light stress study was stopped after 49 days as the discoloration of most of the vials (with a stopper) exceeded the color card scale used to evaluate the discoloration. In some vials the discoloration was out of scale already at the $6^{th}$ week of the experiment (flat oriented vial from batches 1, 5, or 6). As the values are out of the color card scale, the displayed data in the FIG. 2 is limited until day 35.

Prior to the start of the study, the vials were examined for any discoloration (0 time point). All of them did not show any discoloration (color comparable to placebo). As shown in FIG. 2 in all batches that were continuously exposed to light, already after a week a clear change in color was observed. For batch 1, an additional daily test was performed where it was observed that the discoloration already started after 2 days. Additionally, in the vials with the stopper that were continuously exposed to D50 light, after 2 weeks a turbid band on the surface of the glass vial, a yellowish discoloration of the stopper surface and particles could be clearly seen. Yellowish discoloration of the stopper surface and particles could be clearly seen in the vials (here for batch 6) after 2 weeks of D50 light exposure Particles were observed to be visually similar to the ones observed earlier (for batch 1). In the vials that were kept in dark as a reference at room temperature as well as at 70° C., no changes in the color and no particles were observed.

(ii) Influence of initial light exposure followed by storage in dark

Figure 3:
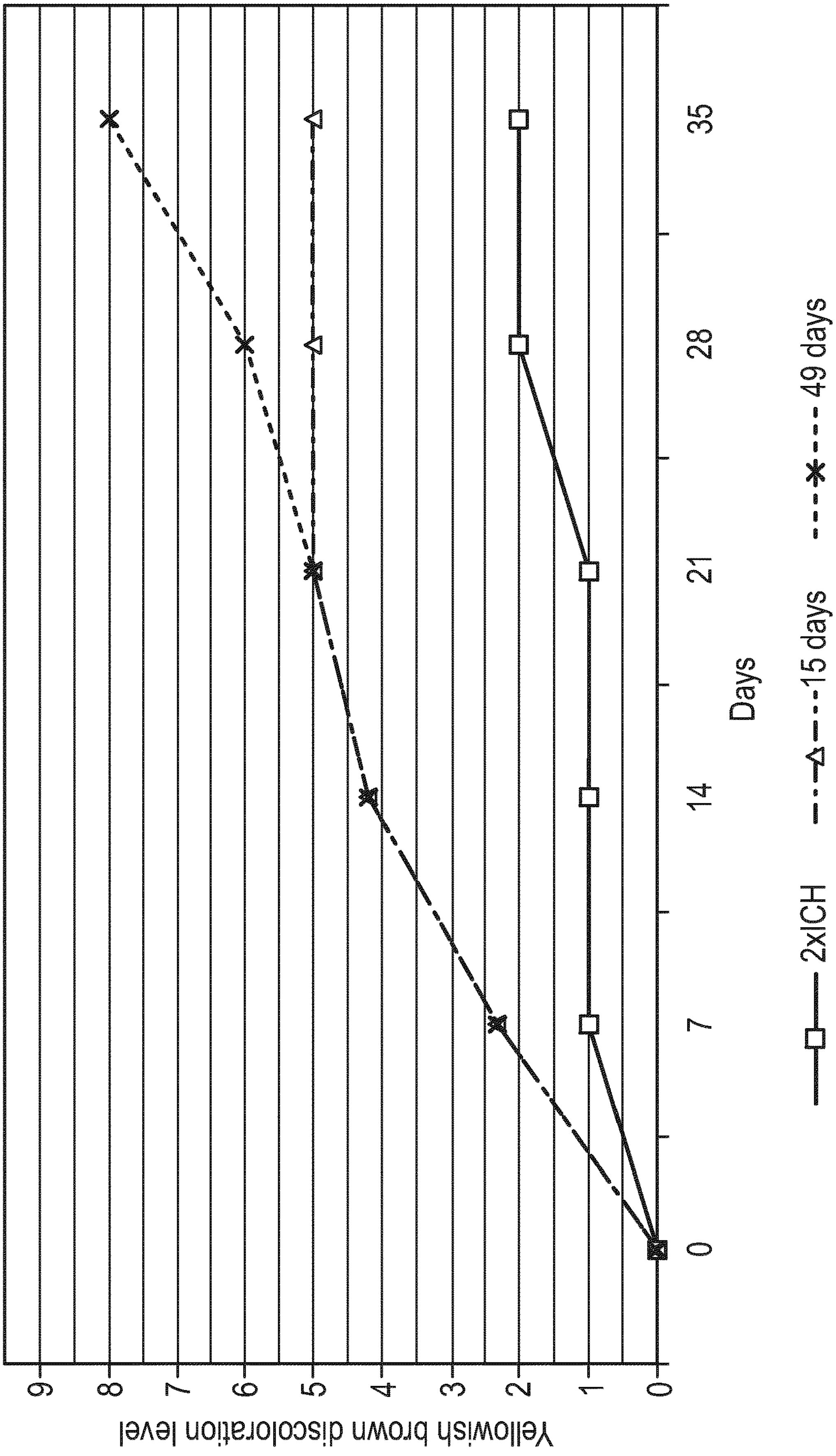
FIG. 3 is line graph comparing color change in vials with stopper exposed to continuous D50 light, and to D50 light for 15 days and to 2 times (16 h) ICH followed by storage in the dark at room temperature for batch 7.

As shown in FIG. 3 the vials exposed to D50 light for 15 days discolored similar as the vials exposed to continuous D50 light, but after putting in dark the color change significantly slowed down (batch 6 behaved very similar to batch 7).

A similar observation can be made for the exposure to ICH light. After exposure to ICH light, the vials showed a slight discoloration (more colored than a placebo vial but less than scale 1 on the color card). After subsequent storage in dark of these ICH stressed samples, the discoloration continued slowly.

(iii) Influence of Temperature of Dark Storage

As shown in FIG. 4, the vials that were exposed to ICH light and then were kept in dark at room temperature slowly continued to discolor at a slow pace while those kept in dark at 70° C. continued to discolor as well, but faster.

(iv) Influence of Light Intensity

The results show that discoloration after 2x ICH is less pronounced than after 7 days of continuous exposure to D50 light despite the fact that the amount of lux hours received is much higher (two cycles of ICH light (2×8 hours) correspond to 2×1.2 million lux hours, while 7 days of D50 light (~210 fc) correspond to only ~400000 lux hours). The intensity of the light therefore seems to be less critical than the duration.

(v) Influence of Vial Orientation and Presence of Stopper

It was observed that flat oriented vials showed a higher discoloration compared to upwards or downwards oriented ones (see an example graph for batch 6 in FIG. 5 (first graph), other batches behaved in similar way). This might be related to the difference in surface area of the product being exposed to light. When vials are lying flat, the full side of the vial can be exposed, while when oriented downward, only the top part is exposed. In case of upward orientation, the stopper may even cast a shadow on the liquid below, thereby partially blocking the light.

The vials that did not contain a stopper discolored slower (see a comparison in FIG. 5 (second graph) of the same oriented vials coming from different batches, and prepared from the same esketamine hydrochloride batch). In the vials without stopper also no particles were observed. This strongly suggests that particle creation is related to the stopper and its contact with esketamine solution in the vial.

D. Identification of the Discoloration

Microscopic images of particles isolated on Anodisc filters from all batches were obtained. The microscopic evaluation indicated that a large number of small brown particle were present in the stressed batches. A few larger brown particles, or possibly agglomerates of smaller particles, were observed also. The appearance of these particles is similar to that of the particles isolated for the discolored retain vials of batch 1.

Particles were further subjected to IR microscopic analysis. Unfortunately, the brown particles could not be identified conclusively. However, significant similarities were observed between the IR spectra that were collected here and those that had previously been obtained for brown particles found in discolored retain vials of batch 1. As in the previous investigation, possible contributions of a silicone-like material, and a number of additional bands which could not be assigned to any specific compounds, were observed to be present in the IR spectra. However, in the spectra of the particles isolated from the vials from the light stress study, the relative contribution of the silicone-like material appeared to be smaller than in the spectra of the particles isolated from the retain vials (batch 1).

Different esketamine batches (1 and 5-7) exposed to light conditions were analyzed by LC-DAD-MS in order to evaluate the impurity profiles. No significant differences were observed by comparing the chromatograms of the different batches exposed to the same conditions.

E. Conclusions of the Light Stress Study

Based on the results of the light stress study, the following observations regarding discoloration can be made:

The behavior of different esketamine drug product batches, including batch 1, under the same light stress conditions is similar (and independent of the metal levels within the ranges studied).

The appearance of light stressed vials is similar to the appearance of the discolored vials (similar appearance of the vial (presence of brown particles, deposit on vial wall and stopper) and similar appearance and chemical composition of the particles).

The duration of the light exposure seems to be more critical than the actual intensity of the light.

After an initial light exposure (leading to discoloration), the discoloration will continue slowly even in absence of light.

Yellow/brown discoloration of vials of esketamine nasal spray 1 is shown to be caused by a combination of silicone particles with yellow/brown material. The yellow/brown material seems to be adsorbed onto the silicone particles and is related to the active pharmaceutical ingredient esketamine.

Aspects of the Invention

1. A pharmaceutical composition comprising esketamine or a pharmaceutically acceptable salt thereof and an oxidative degradant.
2. The pharmaceutical composition of aspect 1, wherein the oxidative degradant is 6-(2-chlorophenyl)-6-oxohexanoic acid or a pharmaceutically acceptable salt thereof.
3. The pharmaceutical composition of aspect 2, comprising not more than 0.2% (HPLC area) of 6-(2-chlorophenyl)-6-oxohexanoic acid or a pharmaceutically acceptable salt thereof, relative to the amount of the esketamine.
4. The pharmaceutical composition of aspect 2, comprising not more than 0.2% (HPLC area) of 6-(2-chlorophenyl)-6-oxohexanoic acid or a pharmaceutically acceptable salt thereof, relative to the amount of esketamine, after storage for at least 6 months, for at least 12 months, for at least 18 months, or for at least 24 months.
5. The pharmaceutical composition of aspect 2, comprising not more than 0.2% (HPLC area) of 6-(2-chlorophenyl)-6-oxohexanoic acid or a pharmaceutically acceptable salt thereof, relative to the amount of esketamine, after storage in the absence of light for at least 6 months, for at least 12 months, for at least 18 months, or for at least 24 months.
6. The pharmaceutical composition of aspect 2, comprising not more than 0.2% w/w of 6-(2-chlorophenyl)-6-oxohexanoic acid or a pharmaceutically acceptable salt thereof, relative to the weight of esketamine.

7. The pharmaceutical composition of aspect 2, comprising not more than 0.2% w/w of 6-(2-chlorophenyl)-6-oxohexanoic acid or a pharmaceutically acceptable salt thereof, relative to the weight of esketamine, after storage for at least 6 months, for at least 12 months, for at least 18 months, or for at least 24 months.
8. The pharmaceutical composition of aspect 2, comprising not more than 0.2% w/w of 6-(2-chlorophenyl)-6-oxohexanoic acid or a pharmaceutically acceptable salt thereof, relative to the weight of esketamine, after storage in the absence of light for at least 12 months, for at least 18 months, or for at least 24 months.
9. The pharmaceutical composition of aspect 2, comprising not more than about 120 ppm of 6-(2-chlorophenyl)-6-oxohexanoic acid or a pharmaceutically acceptable salt thereof.
10. The pharmaceutical composition of aspect 2, comprising not more than about 120 ppm of 6-(2-chlorophenyl)-6-oxohexanoic acid or a pharmaceutically acceptable salt thereof after storage for at least 6 months, for at least 12 months, for at least 18 months, or for at least 24 months.
11. The pharmaceutical composition of aspect 2, comprising not more than about 120 ppm of 6-(2-chlorophenyl)-6-oxohexanoic acid or a pharmaceutically acceptable salt thereof after storage in the absence of light for at least 12 months, for at least 18 months, or for at least 24 months.
12. The pharmaceutical composition of any one of aspects 4, 5, 7, 8, 10, or 11, wherein the storage is at a temperature in the range of about 20° C. to about 75° C.
13. The pharmaceutical composition of aspect 4, 5, 7, 8, 10, or 11, wherein the storage is in an atmosphere having a relative humidity of about 25 to about 80%.
14. The pharmaceutical composition of any one of aspects 3, 6, or 9, wherein the pharmaceutical composition is exposed to light for less than about 1 hour, less than about 30 minutes, less than about 10 minutes, or less than about 1 minute.
15. The pharmaceutical composition of any one of the preceding aspects, wherein the pharmaceutical composition is in a closed container.
16. The pharmaceutical composition of aspect 15, wherein the closed container is a sealed glass vial.
17. The pharmaceutical composition of 15 or 16, wherein the closed container is substantially opaque to light.
18. The pharmaceutical composition of aspect 17, wherein the closed container is an amber container.
19. The pharmaceutical composition of any one of aspects 15 to 18, wherein the closed container comprises a plastic stopper.
20. The pharmaceutical composition of any one of aspects 15 to 19, wherein the closed container is within a second container that is substantially opaque to light.
21. A pharmaceutical composition comprising esketamine or a pharmaceutically acceptable salt thereof and not more than 0.2% (HPLC area) of 6-(2-chlorophenyl)-6-oxohexanoic acid or a pharmaceutically acceptable salt thereof, relative to the amount of the esketamine, after storage in the absence of light for at least 6 months.
22. A pharmaceutical composition comprising esketamine or a pharmaceutically acceptable salt thereof and not more than 0.2% w/w of 6-(2-chlorophenyl)-6-oxohexanoic acid or a pharmaceutically acceptable salt thereof, relative to the weight of the esketamine, after storage in the absence of light for at least 6 months.
23. A pharmaceutical composition comprising esketamine or a pharmaceutically acceptable salt thereof and not more than about 120 ppm of 6-(2-chlorophenyl)-6-oxohexanoic acid or a pharmaceutically acceptable salt thereof after storage in the absence of light for at least 6 months.
24. The pharmaceutical composition of any one of the preceding aspects, that is an intranasal pharmaceutical composition.
25. The pharmaceutical composition of any one of the preceding aspects, further comprising one or more of citric acid monohydrate, edetate disodium, sodium hydroxide, and water.
26. The pharmaceutical composition of any one of the preceding aspects, further comprising not more than about 0.2% (HPLC area) of noresketamine or a pharmaceutically acceptable salt thereof, relative to the amount of the esketamine.
27. A method for preventing the formation of oxidative degradants in a pharmaceutical composition comprising esketamine or a pharmaceutically acceptable salt thereof, comprising one or more of:
    (a) preparing the pharmaceutical composition in the absence of light;
    (b) storing the pharmaceutical composition in the absence of light;
    (c) exposing the pharmaceutical composition to about 6 hours or less of light; or
    (d) filling a container with the pharmaceutical composition in the absence of light.
28. A process for preparing a pharmaceutical composition comprising esketamine or a pharmaceutically acceptable salt thereof and not more than 0.2% (HPLC area) of 6-(2-chlorophenyl)-6-oxohexanoic acid or a pharmaceutically acceptable salt thereof, relative to the amount of esketamine, comprising mixing the esketamine or a pharmaceutically acceptable salt thereof with one or more pharmaceutically acceptable excipients; and exposing the esketamine to about 6 hours or less of light.
29. A process for preparing a pharmaceutical composition comprising esketamine or a pharmaceutically acceptable salt thereof and not more than 0.2% w/w of 6-(2-chlorophenyl)-6-oxohexanoic acid or a pharmaceutically acceptable salt thereof, relative to the weight of esketamine, comprising mixing the esketamine or a pharmaceutically acceptable salt thereof with one or more pharmaceutically acceptable excipients; and exposing the esketamine to about 6 hours or less of light.
30. A process for preparing a pharmaceutical composition comprising esketamine or a pharmaceutically acceptable salt thereof and not more than about 120 ppm of 6-(2-chlorophenyl)-6-oxohexanoic acid or a pharmaceutically acceptable salt thereof, comprising mixing the esketamine or a pharmaceutically acceptable salt thereof with one or more pharmaceutically acceptable excipients; and exposing the esketamine to about 6 hours or less of light.
31. The process of any one of aspects 28 to 30, wherein the mixing is performed using a mixing substrate that is substantially opaque to light.
32. The process of any one of aspects 28 to 30, wherein the mixing substrate comprises a light protective foil.
33. The process of any one of aspects 28 to 32, further comprising filling a container with the pharmaceutical composition.

34. The process of aspect 33, wherein the filling is performed using a filling substrate that is substantially opaque to light.
35. The process of aspect 34, wherein the filling substrate comprises a black silicon sheet or stainless steel.
36. The process of aspect 34 or 35, further comprising covering the container with a second container that is substantially opaque to light.
37. The process of aspect 36, wherein the second container is an aluminum bag.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A method for preventing the formation of oxidative degradants in a pharmaceutical composition comprising esketamine or a pharmaceutically acceptable salt thereof, comprising:

exposing the pharmaceutical composition to 6 hours or less of light during preparation of the composition and filling of a container with the composition; and then storing the pharmaceutical composition in the container, the container having an opacity permitting about 10% or less of light from passing through the container, as measured using an opacimeter.

2. The method of claim 1, wherein the storing is for at least 6 months, for at least 12 months, for at least 18 months, or for at least 24 months.

3. The method of claim 1, wherein the storing is at a temperature in the range of about 20° C. to about 75° C.

4. The method of claim 1, wherein the storing is in an atmosphere having a relative humidity of about 25% to about 80%.

5. The method of claim 1, wherein the container is a sealed glass vial.

6. The method of claim 1, wherein the container is within a second container that has an opacity permitting about 10% or less of light from passing through the container, as measured using an opacimeter.

7. The method of claim 1, wherein the storing is for 6 months at a temperature in the range of about 20° C. to about 75° C., in an atmosphere having a relative humidity of about 25% to about 80%.

8. The method of claim 1, wherein the pharmaceutical composition is an intranasal pharmaceutical composition.

9. The method of claim 1, wherein the pharmaceutical composition further comprises one or more of citric acid monohydrate, edetate disodium, sodium hydroxide, and water.

10. The method of claim 1, comprising exposing the pharmaceutical composition to 1 hour or less of light, during the preparation of the composition and the filling of the container with the composition.

11. The method of claim 1, wherein the preparation comprises mixing the esketamine and one or more pharmaceutically acceptable excipient using a mixing substrate that has an opacity permitting about 10% or less of light from passing through the container, as measured using an opacimeter.

12. The method of claim 11, wherein the mixing substrate comprises a light protective foil.

13. The method of claim 1, wherein the filling is performed using a filling substrate that has an opacity permitting about 10% or less of light from passing through the container, as measured using an opacimeter.

14. The method of claim 13, wherein the filling substrate comprises a black silicon sheet or stainless steel.

15. The method of claim 6, wherein the second container is an aluminum bag.

* * * * *